United States Patent
You et al.

(10) Patent No.: US 10,004,478 B2
(45) Date of Patent: Jun. 26, 2018

(54) METHOD AND APPARATUS FOR DISPLAYING ULTRASOUND IMAGE

(71) Applicant: SAMSUNG MEDISON CO., LTD., Hongcheon-gun, Gangwon-Do (KR)

(72) Inventors: Young-Kwon You, Gangwon-do (KR); Sung-Yoon Kim, Gangwon-do (KR); Jun Kim, Gangwon-do (KR); Gil-Ju Jin, Gangwon-do (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 582 days.

(21) Appl. No.: 14/539,808

(22) Filed: Nov. 12, 2014

(65) Prior Publication Data
US 2015/0141824 A1 May 21, 2015

Related U.S. Application Data

(60) Provisional application No. 61/907,206, filed on Nov. 21, 2013.

(30) Foreign Application Priority Data

Mar. 7, 2014 (KR) .................. 10-2014-0027431

(51) Int. Cl.
*A61B 8/06* (2006.01)
*A61B 8/08* (2006.01)
(Continued)

(52) U.S. Cl.
CPC ............. *A61B 8/488* (2013.01); *A61B 8/06* (2013.01); *A61B 8/461* (2013.01); *A61B 8/463* (2013.01);
(Continued)

(58) Field of Classification Search
CPC ......... A61B 8/488; A61B 8/463; A61B 8/461; A61B 8/465; A61B 8/466; A61B 8/5246; A61B 8/06
See application file for complete search history.

(56) References Cited

U.S. PATENT DOCUMENTS 5,622,173 A * 4/1997 Bisson .................... A61B 8/06
600/459
6,077,226 A 6/2000 Washburn et al.
(Continued)

FOREIGN PATENT DOCUMENTS

CN 101214160 A 7/2008
EP 1 942 352 A2 7/2008
(Continued)

OTHER PUBLICATIONS

Notice of Final Rejection issued in Korean Application No. 10-2014-0027431 dated Jan. 18, 2016, with English translation.
(Continued)

*Primary Examiner* — Jennifer Dieterle
*Assistant Examiner* — Angela M Hoffa
(74) *Attorney, Agent, or Firm* — McDermott Will & Emery LLP

(57) ABSTRACT

A method of displaying an ultrasound image may improve the accuracy of disease diagnosis by enabling a user to recognize an accurate direction of a bloodstream. The method includes: obtaining first Doppler data that is generated by transmitting an ultrasound signal to an object and receiving an echo signal reflected from the object by using a probe; displaying a sound source marker at a first position on a screen; and generating and displaying a first color Doppler image from the first Doppler data in consideration of the first position.

15 Claims, 15 Drawing Sheets

(51) Int. Cl.
*A61B 8/00* (2006.01)
*G06T 11/00* (2006.01)
*G06T 11/60* (2006.01)

(52) U.S. Cl.
CPC ............ *A61B 8/466* (2013.01); *A61B 8/5246* (2013.01); *G06T 11/001* (2013.01); *A61B 8/5223* (2013.01); *A61B 8/565* (2013.01); *G06T 11/60* (2013.01); *G06T 2210/41* (2013.01)

(56) References Cited

U.S. PATENT DOCUMENTS

| | | | |
|---|---|---|---|
| 6,464,642 | B1 | 10/2002 | Kawagishi |
| 7,066,888 | B2 * | 6/2006 | Abend ................. A61B 8/06 600/454 |
| 7,803,112 | B2 | 9/2010 | Kwon |
| 7,806,824 | B2 * | 10/2010 | Ohtake ................. A61B 8/00 600/407 |
| 8,162,837 | B2 * | 4/2012 | Moehring ............. A61B 8/06 600/437 |
| 2002/0151795 | A1 | 10/2002 | Palti |
| 2005/0124885 | A1 | 6/2005 | Abend et al. |
| 2006/0052698 | A1 * | 3/2006 | Loupas ................. A61B 8/06 600/437 |
| 2007/0010747 | A1 | 1/2007 | Sabourin et al. |
| 2008/0167557 | A1 | 7/2008 | Kozai |
| 2010/0099991 | A1 | 4/2010 | Snyder |
| 2010/0222680 | A1 | 9/2010 | Hamada |
| 2011/0196237 | A1 | 8/2011 | Pelissier et al. |
| 2014/0107484 | A1 * | 4/2014 | Hyun ................. G06T 11/206 600/441 |
| 2015/0080735 | A1 * | 3/2015 | Hyun ................. A61B 8/06 600/454 |
| 2015/0148679 | A1 * | 5/2015 | Thiele ................. A61B 8/065 600/454 |
| 2015/0150537 | A1 * | 6/2015 | Maruyama ........... A61B 8/0825 600/407 |
| 2016/0000408 | A1 * | 1/2016 | Matsunaga ............. A61B 8/06 600/441 |

FOREIGN PATENT DOCUMENTS

| | | |
|---|---|---|
| JP | 2001-128975 A | 5/2001 |
| JP | 2004-141523 A | 5/2004 |
| JP | 2005-095278 A | 4/2005 |
| JP | 2008-183396 A | 8/2008 |
| JP | 2010-221011 A | 10/2010 |
| JP | 2012-081167 A | 4/2012 |
| JP | 2013-078396 A | 5/2013 |
| KR | 2005-0069878 A | 7/2005 |
| KR | 10-2014-0047540 A | 4/2014 |

OTHER PUBLICATIONS

Korean Office Action issued in Application No. 10-2016-0032949 dated Apr. 21, 2016, with English translation.
Korean Non-Final Rejection dated Jul. 13, 2015 issued in Korean Patent Application No. 10-2014-0027431 (English translation).
Transmittal of International Search Report and Written Opinion issued in International Application No. PCT/KR2014/010494 dated Feb. 6, 2015.
Korean Office Action issued in Application No. 10-2016-0032949 dated Oct. 27, 2016, with English translation.
Extended Search Report issued in corresponding European Patent Application No. 14863856.2, dated Jul. 11, 2017.
Notice of Allowance issued in corresponding Korean Patent Application No. 10-2016-0032949, dated Jul. 27, 2017, with English Translation.

* cited by examiner

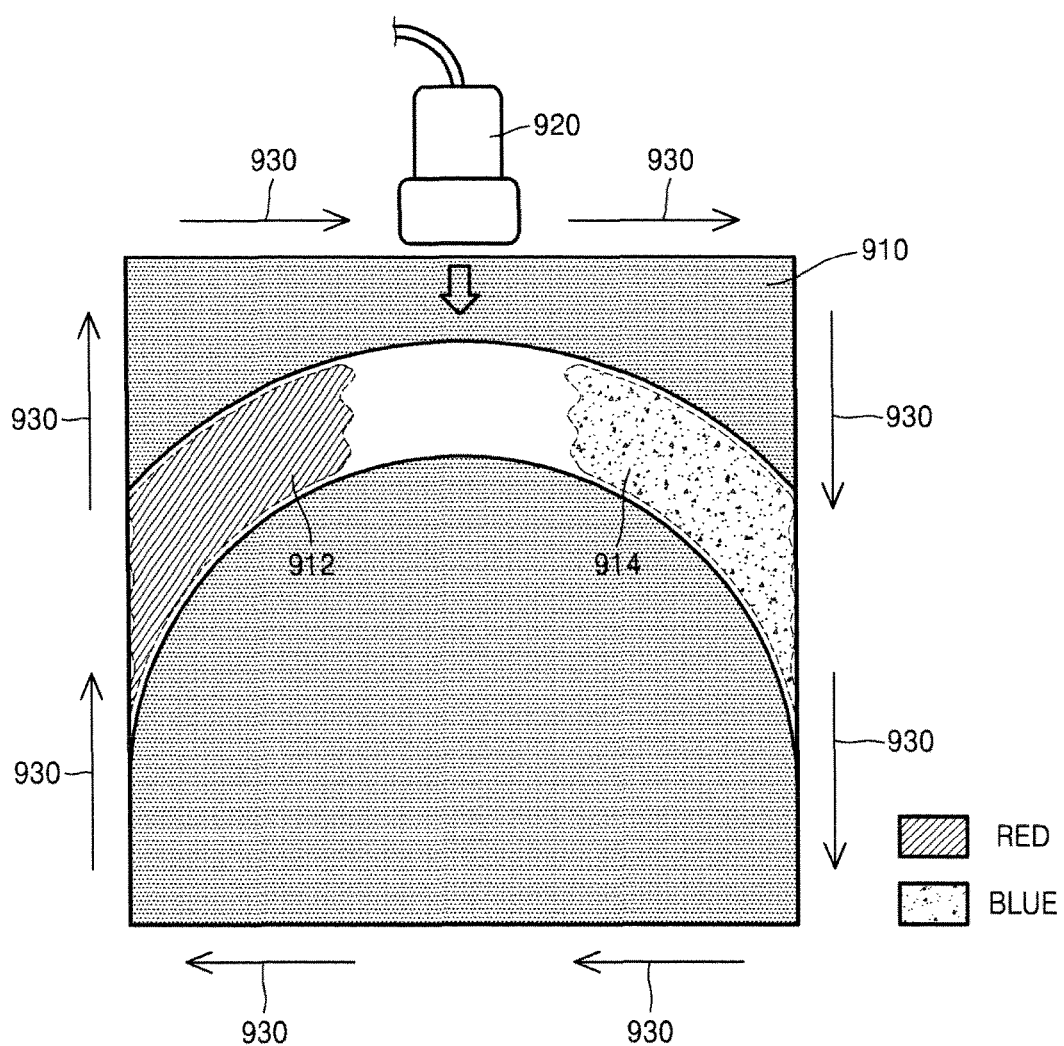

METHOD AND APPARATUS FOR DISPLAYING ULTRASOUND IMAGE

RELATED APPLICATIONS

This application claims the benefit of U.S. Patent Application No. 61/907,206, filed on Nov. 21, 2013, and Korean Patent Application No. 10-2014-0027431, filed on Mar. 7, 2014, in the Korean Intellectual Property Office, the disclosures of which are incorporated herein in their entirety by reference.

BACKGROUND

1. Field

One or more embodiments of the present invention relate to a method and apparatus for displaying an ultrasound image, and more particularly, to a method and apparatus for generating and displaying a color Doppler image that shows a movement of at least a part of an object by using Doppler data.

2. Description of the Related Art

Ultrasound systems have noninvasive and nondestructive characteristics, and thus, are widely used in medical applications for obtaining information about internal body structures of an object. Ultrasound systems may provide medical doctors with high-resolution images of internal body structures of an object without performing surgery involving an incision, and thus, are frequently used in medical applications.

In general, an ultrasound system transmits an ultrasound signal to an object as a probe is brought into contact with a surface of the object and receives an ultrasound signal (hereinafter, referred as an echo signal) reflected from the object. The ultrasound system forms an ultrasound image of the object based on the echo signal received through the probe, and displays the formed ultrasound image on a display.

For example, the ultrasound system may form and display a brightness (B) mode image in which an intensity of the echo signal reflected from the object is expressed by a brightness or a Doppler (D) mode image in which a Doppler component extracted from the echo signal is expressed by a color or a waveform.

In particular, the ultrasound system may generate Doppler data by transmitting an ultrasound signal to the object including a blood vessel through which blood flows and by receiving the echo signal reflected from the object. The ultrasound system may form a color (C) mode image, that is, a color Doppler image, based on the generated Doppler data. The color Doppler image expresses a relative velocity of a bloodstream with respect to a probe by using a color or an arrow. The color Doppler image is widely used to diagnose an occurrence of a cardiac disease.

A general ultrasound system generates a color Doppler image that expresses a relative velocity of a bloodstream with respect to a position of a probe when Doppler data is obtained. When a user using the general ultrasound system manipulates the color Doppler image (for example, when the user moves or rotates the color Doppler image on a screen), the user may not know where the probe is located when the Doppler data is obtained, the location of the probe being a basis of the color Doppler image.

Also, since the general ultrasound system provides the color Doppler image that expresses the relative velocity of the bloodstream with respect to the position of the probe when the Doppler data is obtained, the general ultrasound system may provide a color Doppler image that fails to show an accurate direction of the bloodstream according to a spatial location of the probe.

Accordingly, the user using the general ultrasound system has difficulties in recognizing an accurate direction of the bloodstream which the color Doppler image shows, thereby reducing the accuracy of diagnosis.

SUMMARY

One or more embodiments of the present invention include a method and apparatus for displaying an ultrasound image that provides an accurate direction of a bloodstream to a user in order to increase the accuracy of diagnosing a cardiac disease.

Additional aspects will be set forth in part in the description which follows and, in part, will be apparent from the description, or may be learned by practice of the presented embodiments.

According to one or more embodiments of the present invention, a method of displaying an ultrasound image includes: obtaining first Doppler data that is generated by transmitting an ultrasound signal to an object and receiving an echo signal reflected from the object by using a probe; displaying a sound source marker at a first position on a screen; and generating and displaying a first color Doppler image from the first Doppler data, in consideration of the first position.

The generating and displaying of the first color Doppler image may include: generating second Doppler data from the first Doppler data based on a result of comparison between the first position and a reference position on the screen; and generating the first color Doppler image from the second Doppler data.

The generating of the second Doppler data may include: obtaining an angle between a line that connects the reference position and a predetermined point on the screen and a line that connects the predetermined point and the first position; and generating the second Doppler data by correcting the first Doppler data based on the obtained angle.

The method may further include: moving, based on a user's input, the sound source marker displayed at the first position to a second position; and generating and displaying a second color Doppler image based on the movement of the sound source marker.

The moving of the sound source marker to the second position may include moving the sound source marker from the first position to the second position along a predetermined path on the screen.

The generating and displaying of the second color Doppler image may include: obtaining an angle between a line that connects the first position and a predetermined point on the screen and a line that connects the predetermined point and the second position; and generating the second color Doppler image based on the obtained angle.

The method may further include: transforming a geometry of the first color Doppler image, based on a user's input; and generating and displaying a second color Doppler image based on the transformed geometry of the first color Doppler image.

The transforming of the geometry of the first color Doppler image may include performing at least one of a movement, an expansion, a contraction, and a rotation of the first color Doppler image on the screen.

The screen may include a plurality of areas at which a plurality of Doppler images are displayed, wherein the displaying of the sound source marker at the first position includes displaying a plurality of sound source markers at a plurality of positions of the plurality of areas, respectively, and the generating and displaying of the first color Doppler image includes generating and displaying a plurality of color Doppler images of a plurality of cross-sections of the object from the first Doppler data based on the plurality of positions of the plurality of sound source markers.

The generating and displaying of the first color Doppler image may include: generating a three-dimensional (3D) brightness (B) mode image of at least a part of the object based on volume data of the object; and displaying the first color Doppler image on the 3D B mode image.

The method may further include: moving the sound source maker displayed at the first position to a second position along at least one of an x-axis, a y-axis, and a z-axis of the 3D B mode image based on a user's input; and generating a second color Doppler image based on the movement of the sound source marker and displaying the second color Doppler image on the 3D B mode image.

According to one or more embodiments of the present invention, a method of displaying an ultrasound image includes: obtaining Doppler data that is generated by transmitting an ultrasound signal to an object and receiving an echo signal reflected from the object by using a probe; displaying a color Doppler image by using the Doppler data and displaying the color Doppler image on a screen; and displaying a sound source marker at a first position on the screen corresponding to the color Doppler image, wherein the first position indicates an angle between a direction in which a bloodstream flows in the object and a direction in which the probe receives the echo signal.

According to one or more embodiments of the present invention, an apparatus for displaying an ultrasound image includes: a data obtainer that obtains first Doppler data that is generated by transmitting an ultrasound signal to an object and receiving an echo signal reflected from the object by using a probe; a display that displays a sound source marker at a first position on a screen; and a processor that generates a first color Doppler image from the first Doppler data in consideration of the first position, wherein the display further displays the first color Doppler image.

The processor may generate second Doppler data from the first Doppler data based on a result of comparison between the first position and a reference position on the screen, and generates the first color Doppler image from the second Doppler data.

The processor may obtain an angle between a line that connects the reference position and a predetermined point on the screen and a line that connects the predetermined point and the first position, and generate the second Doppler data by correcting the first Doppler data based on the obtained angle.

The apparatus may further include a user input device that receives a user's input, wherein the processor moves the sound source marker displayed at the first position to a second position based on the user's input, and generates a second color Doppler image based on the movement of the sound source marker, and the display displays the second color Doppler image.

The processor may move the sound source marker from the first position to the second position along a predetermined path on the screen.

The processor may obtain an angle between a line that connects the first position and a predetermined point on the screen and a line that connects the predetermined point and the second position, and generate the second color Doppler image based on the obtained angle.

The apparatus may further include a user input device that receives a user's input, wherein the processor transforms a geometry of the first color Doppler image based on the user's input, and generates a second color Doppler image based on the geometry transformation of the first color Doppler image, and the display displays the second color Doppler image.

The processor may perform at least one of a movement, an expansion, a contraction, and a rotation of the first color Doppler image on the screen.

The display may display a plurality of Doppler images at a plurality of areas on a screen, and display a plurality of sound source markers at a plurality of positions of the plurality of areas, respectively, wherein the processor generates a plurality of color Doppler images of a plurality of cross-sections of the object from the first Doppler data based on the plurality of positions of the plurality of sound source markers.

The processor may further generate a three-dimensional (3D) brightness (B) mode image of at least a part of the object based on volume data of the object, and the display may display the first color Doppler image on the 3D B mode image.

The apparatus may further include a user input device that receives a user's input, wherein the processor moves the sound source marker displayed at the first position to a second position along at least one of an x-axis, a y-axis, and a z-axis of the 3D B mode image, based on the user's input, and generates a second color Doppler image based on the movement of the sound source marker, and the display displays the second color Doppler image on the 3D B mode image.

According to one or more embodiments of the present invention, an apparatus for displaying an ultrasound image includes: a data obtainer that obtains Doppler data that is generated by transmitting an ultrasound signal to an object and receiving an echo signal reflected from the object by using a probe; a processor that generates a color Doppler image by using the Doppler data; and a display that displays the color Doppler image on a screen, and displays a sound source marker at a first position on the screen corresponding to the color Doppler image, wherein the first position indicates an angle between a direction in which a bloodstream flows in the object and a direction in which the probe receives the echo signal.

According to one or more embodiments of the present invention, a computer-readable recording medium has embodied thereon a program for executing the method.

BRIEF DESCRIPTION OF THE DRAWINGS

These and/or other aspects will become apparent and more readily appreciated from the following description of the embodiments, taken in conjunction with the accompanying drawings in which:

FIGS. 9A and 9B are views illustrating movement paths of a sound source marker that is moved on a screen, according to embodiments of the present invention.

DETAILED DESCRIPTION

Figure 1:
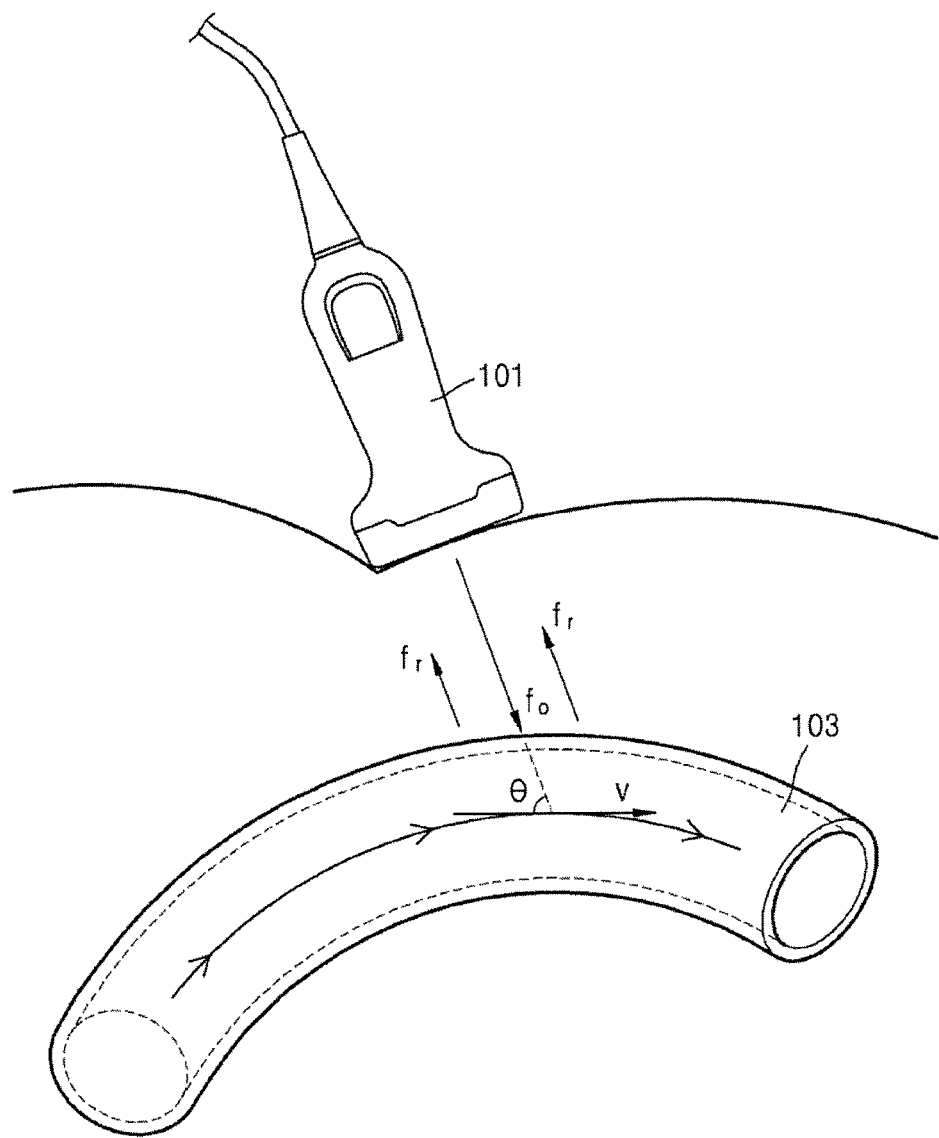
FIG. 1 is a conceptual view for explaining a method of obtaining Doppler data of an object by using a probe in a general ultrasound system.

As used herein, the term "and/or" includes any and all combinations of one or more of the associated listed items. Expressions such as "at least one of," when preceding a list of elements, modify the entire list of elements and do not modify the individual elements of the list.

The present invention will now be described more fully with reference to the accompanying drawings for those of ordinary skill in the art to be able to perform the present invention without any difficulty. The invention may, however, be embodied in many different forms and should not be construed as being limited to the embodiments set forth herein; rather, these embodiments are provided so that this disclosure will be thorough and complete, and will fully convey the concept of the invention to those of ordinary skill in the art. Also, parts in the drawings unrelated to the detailed description are omitted to ensure clarity of the present invention. Like reference numerals in the drawings denote like elements.

Throughout the specification, it will be understood that when an element is referred to as being "connected" to another element, it may be "directly connected" to the other element or "electrically connected" to the other element with intervening elements therebetween. It will be further understood that when a part "includes" or "comprises" an element, unless otherwise defined, the part may further include other elements, not excluding the other elements.

Also, the term "object" used herein may refer to a living object or a non-living object. Also, the object may refer to a body part of a human or an animal. For example, the object may include an organ such as the liver, heart, womb, brain, breast, or stomach, or a fetus. Also, the term "user" used herein may refer to, but is not limited to, a medical expert such as a medical doctor, a nurse, a clinical pathologist, a sonographer, or a medical image expert.

The present invention will now be described more fully with reference to the accompanying drawings, in which exemplary embodiments of the invention are shown.

FIG. 1 is a conceptual view for explaining a method of obtaining Doppler data of an object by using a probe in a general ultrasound system.

The Doppler effect is used in medical ultrasonography to detect a moving reflector (for example, red cells included in blood that flows through a blood vessel), and is also used to characterize and measure a bloodstream. As shown in FIG. 1, due to the Doppler effect, a difference occurs between a frequency fo of an ultrasound signal that is transmitted by a probe 101 and a frequency fr of an echo signal that is received by the probe 101. The difference between the frequency fo of the ultrasound signal that is transmitted by the probe 1010 and the frequency fr of the echo signal that is received by the probe 101 is referred to as a Doppler deflection frequency fd.

The Doppler deflection frequency fd is proportional to a velocity of the reflector that reflects the ultrasound signal, and is also proportional to a cosine value of an angle θ between a direction in which the echo signal reflected from the reflector is received and a direction in which the reflector moves.

In detail, the Doppler deflection frequency fd may be defined as follows.

$$f_d = f_r - f_o = \frac{(2f_o v \cos\theta)}{c}. \quad (1)$$

In Equation 1, fo is a transmission frequency, fr is a reception frequency, v is a velocity of a reflector, and c is a sound velocity in a living body, θ is a Doppler angle (or an angle at which an ultrasound signal is incident), and is an angle between a direction in which an echo signal reflected from a reflector is received and a direction in which the reflector moves. The Doppler angle θ may be input by a user or a measured by a probe.

The general ultrasound system generates Doppler data of the object by using the echo signal received by the probe 101. The Doppler data of the object includes information about a movement of the reflector that moves in the object. The information about the movement of the reflector may include a relative velocity of the reflector with respect to the probe 101.

In detail, the general ultrasound system obtains the relative velocity v of the reflector with respect to the probe 101 that receives the ultrasound signal by using the echo signal. The relative velocity v of the reflector may be obtained according to Equation 1 based on the Doppler deflection frequency fd and the Doppler angle θ. The ultrasound signal of the transmission frequency fo that is already known may be transmitted, and the reception frequency fr of the ultrasound signal that is received from the reflector in response to the transmitted ultrasound signal may be detected. The Doppler deflection frequency fd may be calculated based on the transmission frequency fo and the reception frequency fr. Accordingly, assuming that the sound velocity c is constant in Equation 1, the relative velocity v of the reflector may be calculated by measuring the Doppler deflection frequency fd and cos θ.

The general ultrasound system may generate a color Doppler image to which at least one color selected according to the information about the movement of the reflector is allocated. For example, the general ultrasound system may store a color map in which a plurality of colors are mapped to a plurality of relative velocities. The general ultrasound system may extract from Doppler data a relative velocity of a predetermined region of the object corresponding to each pixel of the Doppler image, and may generate a color Doppler image by allocating at least one color that is selected based on the extracted relative velocity and the stored color map to each pixel.

A color image that is to overlap with a black-and-white image of the object may be provided in a color Doppler mode of the general ultrasound system that provides the color Doppler image. For example, the general ultrasound system may display the color Doppler image on a corresponding area of a black-and-white brightness (B) mode image of the object. That is, the color Doppler image (for example, a color Doppler image displaying a velocity of the blood flowing in the blood vessel) corresponding to the part of the object may be displayed on an area of a B mode image corresponding to a part (for example, the inside of a blood vessel in which blood flows) of the object that moves.

For example, the color Doppler image may express a direction and a velocity of a bloodstream that flows in the object. The color Doppler image may express a direction of the bloodstream by using a color, and may also express a velocity of the bloodstream by using a luminance.

Figure 2A:
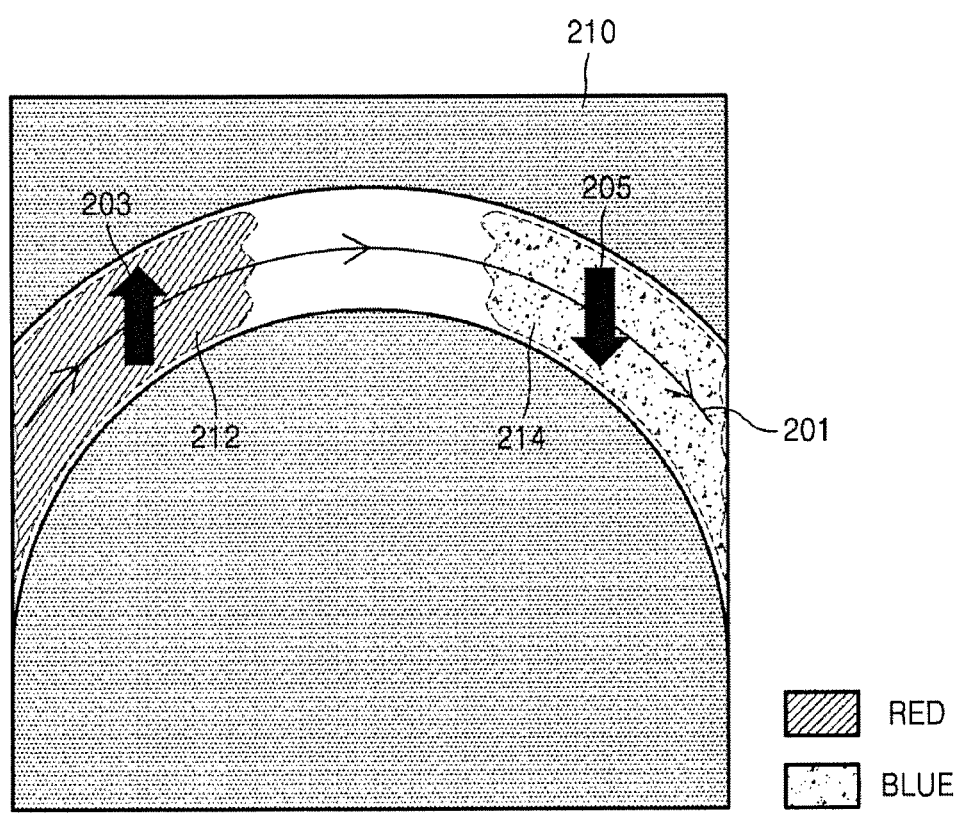
FIGS. 2A and 2B are color Doppler images provided by the general ultrasound system of FIG. 1.
Figure 2B:
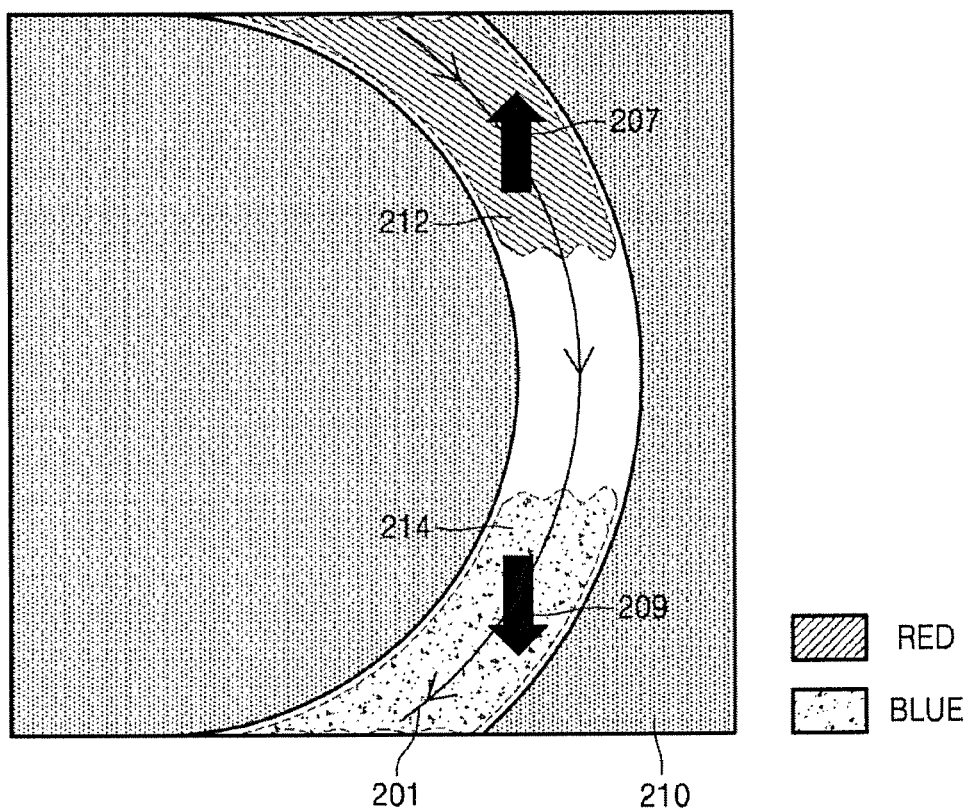

FIGS. 2A and 2B are color Doppler images that are provided by the general ultrasound system of FIG. 1.

In FIGS. 2A and 2B, an image 210 is a B mode image of the object, an arrow 201 indicates an actual direction of the bloodstream that flows in the object, and images 212 and 214 are color Doppler images. The arrow 201 and arrows 203 and 205 are not shown in a general color Doppler image, but are shown herein for a better understanding of the present invention.

As shown in FIG. 2A, the general ultrasound system may provide the color Doppler images 212 and 214 that include information about the bloodstream that flows in the object by using at least one color. The general ultrasound system may display the color Doppler images 212 and 214 on an area corresponding to the bloodstream of the B mode image 210 as shown in FIG. 2A.

The general ultrasound system provides a color Doppler image that expresses a relative velocity of the bloodstream, based on an upper side of the B mode image 210. As shown in FIG. 2A, the general ultrasound system may provide the color Doppler image 212 that expresses the bloodstream moving toward the probe 101 by using a red color. Also, the general ultrasound system may provide the color Doppler image 214 that expresses the bloodstream moving away from the probe 101 by using a blue color.

Also, the general ultrasound system does not display on a screen a color Doppler image of a region of the object which forms an angle of 90° between the ultrasound signal transmitted/received by the probe 101 and the bloodstream. This is because the bloodstream forming the angle of 90° from the ultrasound signal transmitted/received by the probe 101 has a relative velocity of 0 with respect to the probe 101.

As described above, since the arrow 201 that indicates the actual direction of the bloodstream flowing in the object is not actually shown on the color Doppler image displayed by the general ultrasound system, the user predicts a direction of the bloodstream based on at least one color expressed by the color Doppler image.

The user may determine based on the color Doppler image 212 that is shown in red that the direction of the bloodstream corresponding to the color Doppler image 212 is a direction in which the bloodstream moves toward the upper side of the B mode image 210 as indicated by the arrow 203. Also, the user may determine based on the color Doppler image 214 that is shown in blue that the direction of the bloodstream corresponding to the color Doppler image 214 is a direction in which the bloodstream moves away from the upper side of the B mode image 210 as indicated by the arrow 205.

As shown in FIG. 2A, the general ultrasound system provides to the user a color Doppler image expressing a relative velocity of a bloodstream based on an upper side of an image. Accordingly, when the user manipulates the color Doppler image (for example, when the user rotates or expands the color Doppler image), the user has difficulties in recognizing a direction of the bloodstream by using only the color Doppler image. This is because in the general ultrasound system, when the user manipulates the color Doppler image, the user does not know a reference point with respect to which the color Doppler image expresses a relative velocity of the bloodstream. Problems in the use of the general ultrasound system will now be explained in detail with reference to FIG. 2B.

FIG. 2B illustrates a case where the B mode image 210 and the color Doppler images 212 and 214 of FIG. 2A are rotated clockwise by 90°.

When an image is rotated as shown in FIG. 2B, the user still analyzes the color Doppler images 212 and 214 based on the upper side of the B mode image 210.

The user may determine that the direction of the bloodstream corresponding to the color Doppler image 212 is a direction in which the bloodstream moves toward the upper side of the B mode image 210 as indicated by an arrow 207. Also, the user may determine based on the color Doppler image 214 that is shown in blue that the direction of the bloodstream corresponding to the color Doppler image 214 is a direction in which the bloodstream moves away from the upper side of the B mode image 210 as indicated by an arrow 209.

Accordingly, the direction of the bloodstream recognized by the user by using the color Doppler images 212 and 214 of FIG. 2B is different from the actual direction of the bloodstream indicated by the arrow 201. As shown in FIG. 2B, according to the general ultrasound system, when the user manipulates a color Doppler image, the user may not obtain accurate information about a movement of a bloodstream. That is, there is a difference between an actual direction of the bloodstream and a direction of the bloodstream recognized by the user by using the color Doppler image.

In particular, when a second user loads a color Doppler image that is stored after being manipulated by a first user, the second user may have difficulties in intuitively recognizing a direction of a bloodstream expressed by the loaded color Doppler image.

Considering the problems of a conventional method of displaying a color Doppler image which expresses a relative velocity of a bloodstream with respect to a position of a probe based on an upper side of a screen when Doppler data is obtained, the present invention provides a method and apparatus for displaying an ultrasound image which enables a user to recognize an accurate direction of a bloodstream.

In detail, the method and apparatus of the present invention may display a color Doppler image and a sound source marker that indicates a reference point of the color Doppler image. Also, the method and apparatus of the present invention may provide a color Doppler image that shows information about a bloodstream via a simple manipulation by processing Doppler data and generating a color Doppler image from the processed Doppler data based on geometry transformation of the color Doppler image.

Figure 3A:
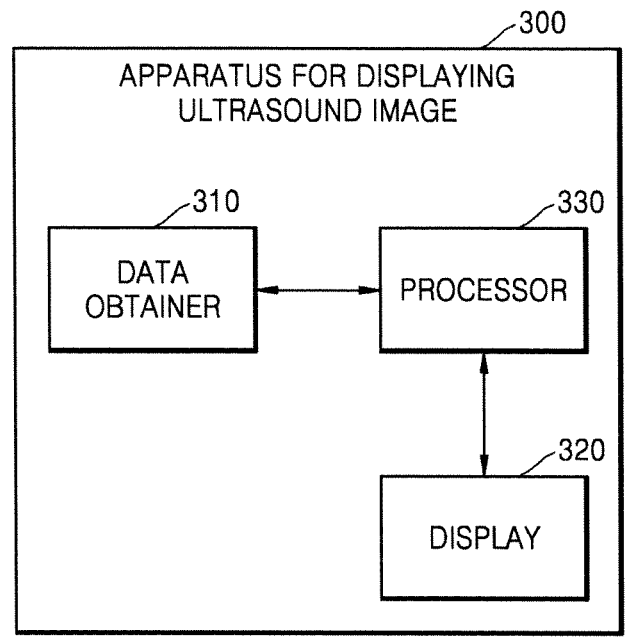
FIGS. 3A and 3B are block diagrams illustrating an apparatus for displaying an ultrasound image, according to an embodiment of the present invention.
Figure 3B:
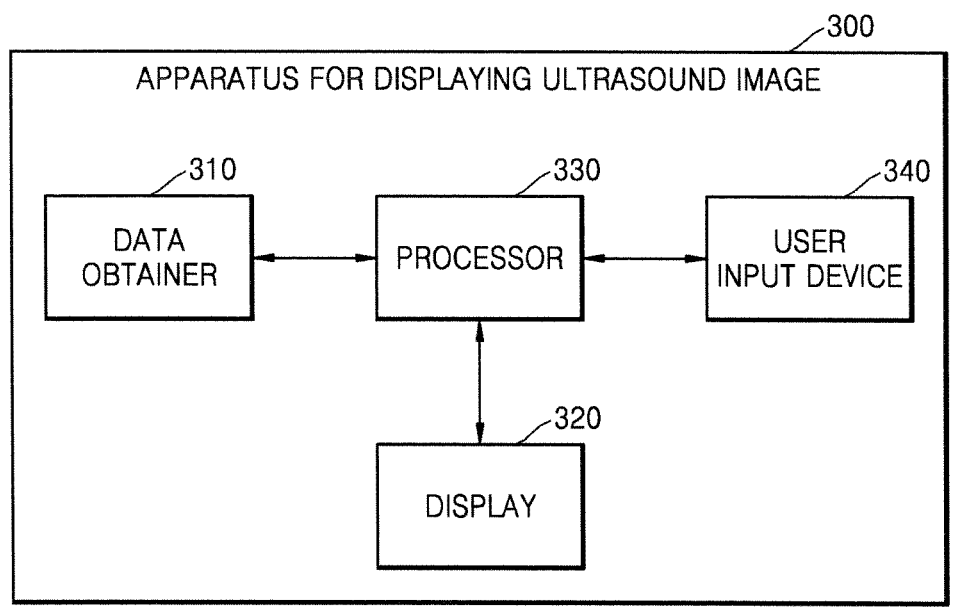

FIGS. 3A and 3B are block diagrams illustrating an apparatus 300 for displaying an ultrasound image, according to an embodiment of the present invention.

As shown in FIG. 3A, the apparatus 300 includes a data obtainer 310, a processor 330, and a display 320.

The apparatus 300 of FIGS. 3A and 3B may be of a cart type or a portable type. Examples of a portable ultrasound diagnostic device may include, but are not limited to, a picture archiving and communication system (PACS) viewer, a smart phone, a laptop computer, a personal digital assistant (PDA), and a tablet PC.

The data obtainer 310 obtains Doppler data of an object. The Doppler data obtained by the data obtainer 310 may be data that is generated by transmitting an ultrasound signal to the object and receiving an echo signal reflected from the object by using a probe. The Doppler data may include information about a movement (for example, the flow of blood in the object) of at least a part of the object. For example, the information about the movement may include a velocity and a direction of the movement.

For example, the data obtainer 310 may include the probe so that the probe transmits/receives an ultrasound signal to/from the object.

The probe may transmit the ultrasound signal to the object, and may receive an echo signal reflected from the object in response to the ultrasound signal. The probe may transmit the ultrasound signal to the object according to a driving signal that is applied to the probe, and may receive the echo signal reflected from the object.

The probe includes a plurality of transducers, and the plurality of transducers oscillate according to an electrical signal transmitted thereto and generate ultrasound signals. Also, the probe may be wirelessly or wiredly connected to a main body of the apparatus 300, and the apparatus 300 may include a plurality of the probes according to its type. Examples of the data obtainer 310 of FIGS. 3A and 3B may include a 1D probe, a 1.5 D probe, and a matrix 2D probe.

The ultrasound signal transmitted from the probe may be a defocused ultrasound signal or a focused ultrasound signal. That is, examples of the ultrasound signal (ultrasound beam) transmitted from the probe include a general focused ultrasound beam whose focal point is located inside an imaging area, a broad ultrasound beam whose a focal point is located outside an imaging area, a plane-wave ultrasound beam whose focal point is located at an infinite distance, and a virtual apex ultrasound beam whose focal point is located behind a surface of an ultrasound probe.

For example, the probe include in the data obtainer 310 of FIGS. 3A and 3B may transmit the ultrasound signal that is a plane-wave signal to the object, and may receive the echo signal reflected from the object in response to the transmitted ultrasound signal. A method of quickly obtaining Doppler data of a wide region of the object by using an ultrasound signal that is a plane-wave signal is referred to as an ultrafast Doppler imaging method.

The data obtainer 310 may further include a data generater that obtains the Doppler data from the echo signal received from the probe. In this case, the data obtainer 310 may obtain real-time Doppler data from the object by continuously transmitting the ultrasound signal to the object and receiving the echo signal, and may output the obtained real-time Doppler data to the processor 330.

Alternatively, the data obtainer 310 may receive from the outside the Doppler data of the object, or may obtain the Doppler data from a storage unit (not shown) that is disposed inside the data obtainer 310. The data obtainer 310 may obtain the Doppler data from an external device that is wirelessly or wiredly connected to the apparatus 300.

The display 320 displays a sound source marker at a first position on a screen.

The sound source marker is an icon indicating a sound source that transmits the ultrasound signal to the object and receives the echo signal in order to obtain a color Doppler image. The sound source marker according to an embodiment of the present invention may indicate a position and a direction which is a basis for identifying the color Doppler image by being displayed on the screen along with the color Doppler image. The sound source marker may be an icon including at least one of a text, a figure, and an image. For example, the sound source maker may be an icon having a probe-like shape or an icon having an arrow shape in order to be intuitively recognized by a user.

The display 320 further displays a first color Doppler image along with the sound source marker. In this case, the first color Doppler image is a color Doppler image that is generated by the processor 330 in consideration of the first position. Also, the display 320 may display a second color Doppler image that is generated based on geometry transformation of the first color Doppler image or a movement of the sound source marker. The processor 330 may generate the first color Doppler image by using first Doppler data that is obtained by the data obtainer 310. In this case, the processor 330 may generate the first color Doppler image in consideration of the first position of the sound source marker displayed on the screen.

The processor 330 may generate the color Doppler image by performing scan conversion on the generated Doppler data.

Also, the processor 330 may generate an ultrasound image of any of various modes in addition to the Doppler image. The ultrasound image may include at least one of an amplitude (A) mode image, a B mode image, and a motion (M) mode image. Also, the processor 330 may generate volume data by processing the echo signal, and may generate a three-dimensional (3D) ultrasound image by performing volume rendering on the volume data. Also, the processor 330 may further generate an elasticity image that images a degree of deformation of the object according to pressure, and may express various pieces of additional information via text or graphics on the ultrasound image.

The processor 330 may generate the sound source marker that is displayed on the screen along with the first color Doppler image. The sound source marker that is generated by the processor 330 may be displayed at the first position on the screen. In this case, the first position may be determined based on a value that is previously stored in the first Doppler data that is used to generate the first color Doppler image or may be determined by the user's input. For example, the first position may be a position on the screen indicating an angle between a direction in which a bloodstream flows in the object and a direction in which the probe receives the echo signal, when the probe transmits the ultrasound signal to the object and receives the echo signal in order to generate the Doppler data.

The processor 330 may update and display the color Doppler image based on geometry transformation of the color Doppler image or a movement of the sound source marker.

For example, the processor 330 may move, based on the user's input that is received by a user input device 340, the sound source marker that is displayed at the first position to a second position. The processor 330 may generate a second color Doppler image based on the movement of the sound source marker.

Alternatively, the processor 330 may transform a geometry of the first color Doppler image based on the user's input that is received by the user input device 340. When the processor 330 transforms the geometry of the first color Doppler image, the processor 330 may perform at least one of a movement, an expansion, a contraction, and a rotation of the first color Doppler image on the screen. The processor 330 may generate the second color Doppler image based on the geometry transformation of the first color Doppler image.

The apparatus 300 of FIGS. 3A and 3B may display the sound source marker, and may generate and display the color Doppler image in consideration of a position at which the sound source marker is displayed.

Alternatively, the apparatus 300 may display the color Doppler image, and may display the sound source marker at a position corresponding to the color Doppler image. The position corresponding to the color Doppler image may be a position indicating an angle between the direction in which the bloodstream flows in the object and the direction in which the probe receives the echo signal.

The display 320 may display the sound source marker at a position on the screen corresponding to a position in an actual space of the probe that transmits/receives the ultrasound signal in order to generate the Doppler data. Since the apparatus 300 of FIGS. 3A and 3B provides the first color Doppler image and the sound source marker on the screen, the user may interpret the first color Doppler image based on the sound source marker, and may know a relative velocity of the bloodstream.

Also, the display 320 may display the sound source marker that is moved from the first position to the second position. The display 320 may display the second color Doppler image that is generated based on the movement of the sound source marker.

Also, the display 320 may display the first color Doppler image whose geometry is transformed. The display 320 may display the second color Doppler image that is generated based on the geometry transformation of the first color Doppler image.

The display 320 may display and output various pieces of information processed by the apparatus 300 as well as the color Doppler image on the screen through a graphic user interface (GUI). The apparatus 300 may include two or more displays 320 according to its type.

As shown in FIG. 3B, the apparatus 300 may further include a user input device 340.

The user input device 340 inputs the user's input. The user input device 340 refers to a device by which the user inputs data for controlling the apparatus 300. Examples of the user input device 340 may include, but are not limited to, a keypad, a dome switch, a touchpad (e.g., a contact capacitive type, a pressure resistive overlay type, an infrared beam type, a surface acoustic wave type, an integral strain gauge type, or a piezoelectric type), a jog wheel, and a jog switch. Also, a touchpad that is layered with a display panel of the display 320 may be referred to as a touch screen.

The user input device 340 may receive the user's input for moving the sound source marker displayed on the screen. Also, the user input device 140 may receive the user's input for transforming the geometry of the first color Doppler image displayed on the screen.

The processor 330 may generate the second color Doppler image, based on the user's input for transforming the geometry of the first color Doppler image or the user's input for moving the sound marker, and may display the second color Doppler image instead of the first color Doppler image.

As described above, since the apparatus 300 of FIGS. 3A and 3B displays the sound source marker along with the color Doppler image on the screen, a position and a direction which become a basis for identifying the color Doppler image may be provided to the user by using the sound source marker. The user may recognize an accurate direction of the bloodstream expressed by the color Doppler image by interpreting the color Doppler image based on the sound source marker.

Also, since the apparatus 300 of FIGS. 3A and 3B updates and displays the color Doppler image based on the geometry transformation of the color Doppler image or the movement of the sound source marker, the user may intuitively recognize information about the bloodstream in a desired view.

The term "view" may refer to a method by which the apparatus 300 displays an image of the object on the screen in order to diagnose an anatomical disorder of the object or analyze a movement of the object. There may be various views according to which cross-section image of the object is displayed on the screen or according to how many cross-sectional images of the object are displayed on the screen. For example, in order to diagnose the heart, examples of a standard diagnosis view recommended by the Heart Association may include a long-axis view, a short-axis view, and a four-chamber view.

A conventional ultrasound system provides a color Doppler image that depends on a spatial location of a probe. Accordingly, according to the conventional ultrasound system, a user has to inconveniently move the probe in order to display a color Doppler image where information about a bloodstream is well shown in a desired view.

However, according to the present embodiment, the Doppler data is processed based on the geometry transformation of the color Doppler image or the movement of the sound source marker and the color Doppler image is generated from the processed Doppler data. Thus, according to the present embodiment, the color Doppler image where information about the bloodstream is well shown may be provided via a simple manipulation.

A method performed by the apparatus 300 of FIGS. 3A and 3B to display an ultrasound image will now be explained in detail with reference to FIGS. 4A and 4B.

Figure 4A:
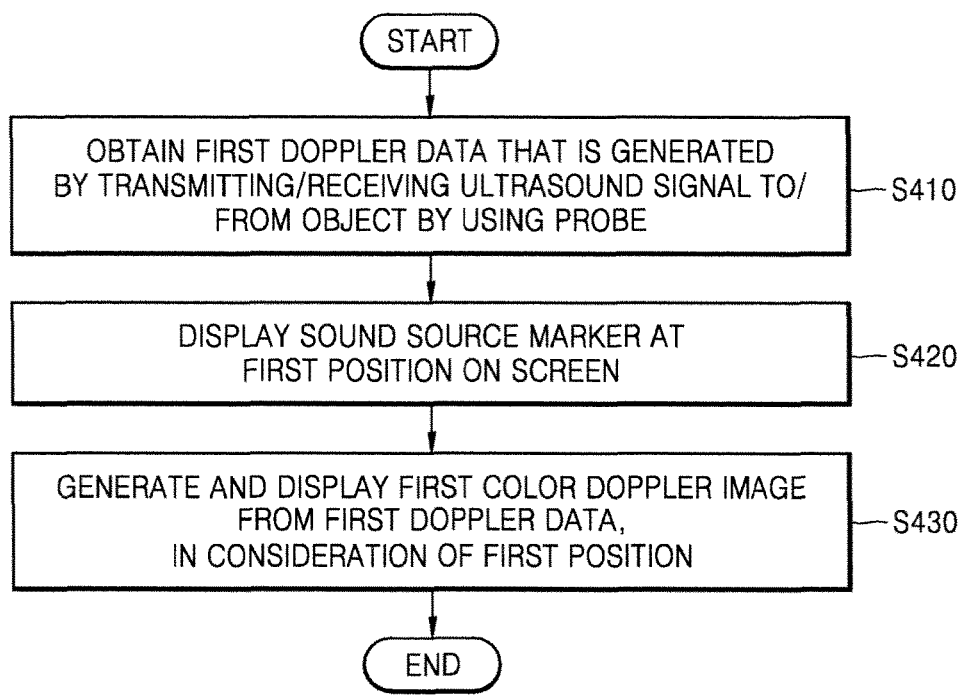
FIGS. 4A and 4B are flowcharts of a method of displaying an ultrasound image, according to embodiments of the present invention.
Figure 4B:
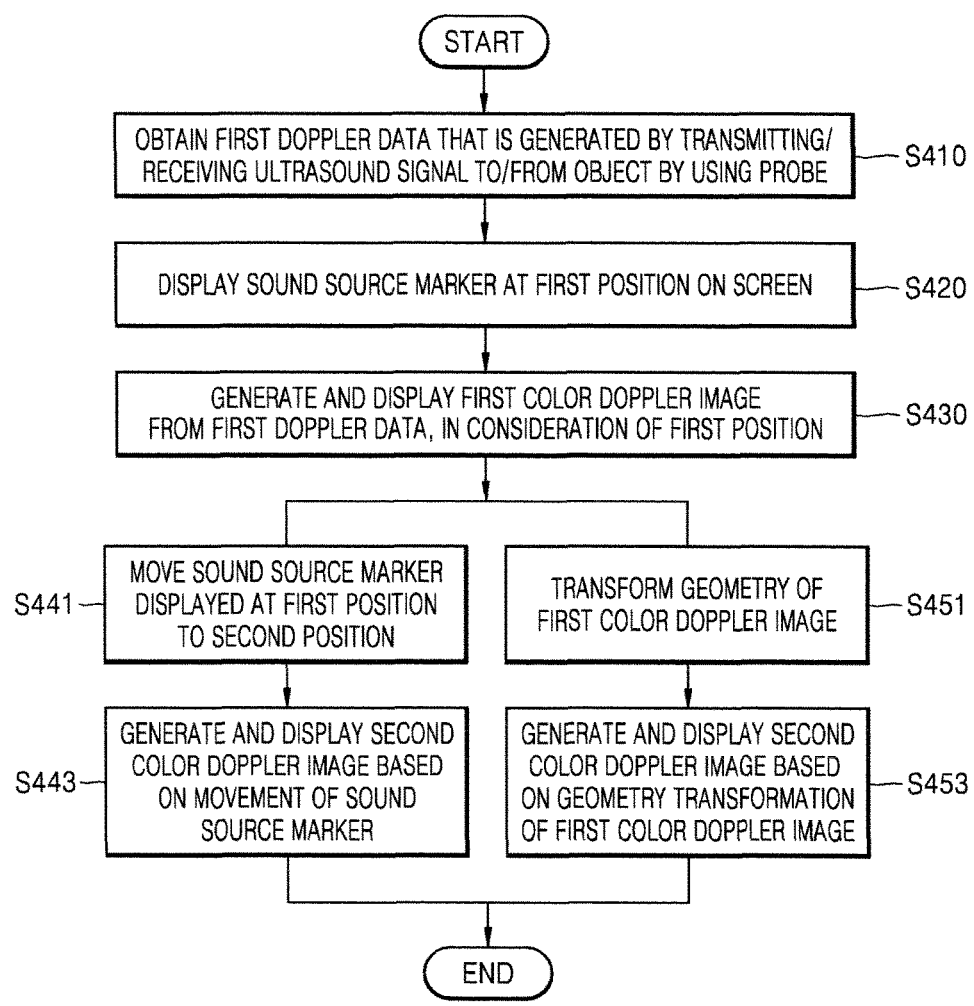

FIGS. 4A and 4B are flowcharts of methods of displaying an ultrasound image, according to embodiments of the present invention.

In operation S410, the apparatus 300 obtains Doppler data of an object. The Doppler data obtained by the apparatus 300 is data that is generated by transmitting an ultrasound signal to the object and receiving an echo signal reflected from the object by using a probe.

The apparatus 300 may include a probe which transmits the ultrasound signal to the object and receives the echo signal from the object and generate the Doppler data. Accordingly, the apparatus 300 may generate real-time Doppler data by continuously transmitting/receiving the ultrasound signal to/from the object. The term "real time Doppler data" regarding data generated and output at the same velocity as a velocity at which a state of the object, such as a movement of the object, is changed refers to Doppler data including a plurality of continuous image frames according to time.

Alternatively, the apparatus 300 may obtain the Doppler data from receiving the Doppler data that is previously stored from the outside or from a memory that is disposed in the apparatus 300.

In operation S420, the apparatus 300 displays a sound source marker at a first position on a screen.

The sound source marker is an icon indicating a sound source that transmits/receives the ultrasound signal to/from the object in order to obtain a color Doppler image. For example, as shown in FIGS. 6A, 6B, 7A, and 7B, the sound source marker may include an image having an ultrasound probe-like shape. However, the present embodiment is not limited thereto, and the sound source marker may include a figure such as an arrow or may include text indicating a position or a direction on the screen.

As will be described below with reference to FIG. 4B, the sound source marker may be used to receive a user's input for updating the color Doppler image. The user may input to the apparatus 300 a command for changing a first color Doppler image that is displayed to a second color Doppler image.

The apparatus 300 may determine the first position on the screen based on a value that is previously stored or the user's input, and may display the sound source marker at the determined first position. The value that is previously stored used to determine the first position may be, for example, a default value that is stored in the apparatus 300, or a value that is stored in the Doppler data that is obtained in operation S410.

In operation S430, the apparatus 300 generates and displays the first color Doppler image from first Doppler data in consideration of the first position.

In FIGS. 4A and 4B, the apparatus 300 may generate second Doppler data from the first Doppler data based on a result of comparison between the first position and a reference position on the screen. The apparatus 300 may generate the first color Doppler image from the generated second Doppler data. The reference position may be a position that is determined based on the user's input, or a position that is previously stored in the apparatus 300. For example, the reference position may be a center of a top surface of an area where the color Doppler image is to be displayed.

In detail, the apparatus 300 may obtain an angle between a line that connects the reference position and a predetermined point on the screen and a line that connects the first position and the predetermined point. The apparatus 300 may generate the second Doppler data by correcting the first Doppler data based on the obtained angle. In this case, the predetermined point on the screen may be determined based on the user's input, or may be determined by a value that is previously stored in the apparatus 300. For example, the apparatus 300 may determine a center of the screen or a center of the color Doppler image as the predetermined point.

For example, the apparatus 300 may correct, by using the following equations, the first Doppler data based on a result of comparison between the reference position and the first position of the sound source marker.

First, a relative velocity $V_1$ of a bloodstream that flows in the object, included in the first Doppler data may be defined by Equation 2. Equation 2 may be derived from Equation 1 that is related to the Doppler effect.

$$V_1 = \frac{cf_d}{2f_o\cos\theta}. \quad (2)$$

In Equation 2, fo is a transmission frequency, fd is a Doppler deflection frequency, and c is a sound velocity. A Doppler angle θ refers to an angle between a direction in which an echo signal reflected from a reflector is received and a direction in which the reflector moves. The Doppler angle θ may be a value that is input by the user or a value that is measured by the probe.

In FIGS. 4A and 4B, the apparatus 300 may compare the first position of the sound source marker with the reference position on the screen, and may obtain a correction angle for correcting the color Doppler data. For example, the apparatus 300 may obtain, but is not limited to, an angle between the line that connects the reference position and the predetermined point on the screen and the line that connects the predetermined point and the first connection as the correction angle.

When the obtained correction angle is $\theta_{adjust}$, a relative velocity $V_2$ of the bloodstream included in the second Doppler data that is generated by correcting the first Doppler data may be derived according to Equation 3 from the relative velocity $V_1$ of the bloodstream included in the first Doppler data.

$$V_2 = \frac{cf_d}{2f_o\cos(\theta - \theta_{adjust})} = V_1 \frac{\cos(\theta)}{\cos(\theta - \theta_{adjust})} \quad \text{(Equation 3)}$$

In Equation 3, fo is a transmission frequency, fd is a Doppler deflection frequency, and c is a sound velocity. A Doppler angle θ refers to an angle between a direction in which the echo signal reflected from the reflector is received and a direction in which the reflector moves. The Doppler angle θ may be a value that is input by the user, or a value that is measured by the probe. $V_1$ is a relative velocity of the bloodstream that is included in the first Doppler data.

Also, in FIGS. 4A and 4B, the apparatus 300 may correct an error by using interpolation processing when generating the color Doppler image from the Doppler data. That is, when the Doppler angle is equal to or greater than 60°, a displacement of a cos curve according to a change of the Doppler angle is greater than that when the Doppler angle is less than 60°. Accordingly, when the Doppler angle at which the ultrasound signal is incident on the predetermined point of the object is equal to or greater than a predetermined angle (for example, 60°), the apparatus 300 may correct an error of an obtained velocity value corresponding to the predetermined point by using velocity values corresponding to neighborhood points around the predetermined point. For example, the apparatus 300 may determine a velocity value that is calculated by interpolating the velocity values around the predetermined point as a velocity value of the predetermined point.

When the Doppler angle at which the ultrasound signal is incident on the predetermined point of the object is 90°, a relative velocity of the predetermined point is 0. Accordingly, a color Doppler image of the predetermined point does not have any color. In this case, in order to determine whether blood flows in the predetermined point (that is, in order to determine whether blood does not flow in the predetermined point and flows at 90° with respect to the ultrasound signal), power data including information about the amount of the bloodstream may be used.

The apparatus 300 according to the present embodiment may detect a region in the object where blood flows in consideration of the power data, may generate a color Doppler image of the region where the blood is detected to flow, and may display the color Doppler image on the screen. The apparatus 300 may display a plurality of color Doppler images of a plurality of cross-sections of the object. The apparatus 300 may display a plurality of color Doppler images of preset standard cross-sections of the object. For example, the apparatus 300 may display color Doppler images showing a coronal plane, a sagittal plane, and an axial plane of the object.

The apparatus 300 may output a plurality of areas that may display a plurality of Doppler images to the screen. The apparatus 300 may display one of a plurality of sound source markers at a predetermined position of each of the plurality of areas. The apparatus 300 may generate and display a plurality of color Doppler images of a plurality of cross-sections of the object based on the predetermined position of each area where each of the plurality of sound source markers is displayed. Alternatively, the apparatus 300 may display a plurality of color Doppler images in a plurality of areas of the screen, and may display a sound source marker in each of the areas corresponding to each of the color Doppler images.

Also, the apparatus 300 may generate and display a 3D B mode image of at least a part of the object based on volume data of the object. The apparatus 300 may display a first color Doppler image on the 3D B mode image that is displayed on the screen. The volume data that is used to generate the 3D B mode image may be ultrasound volume data that is obtained by using the probe.

Figure 6A:
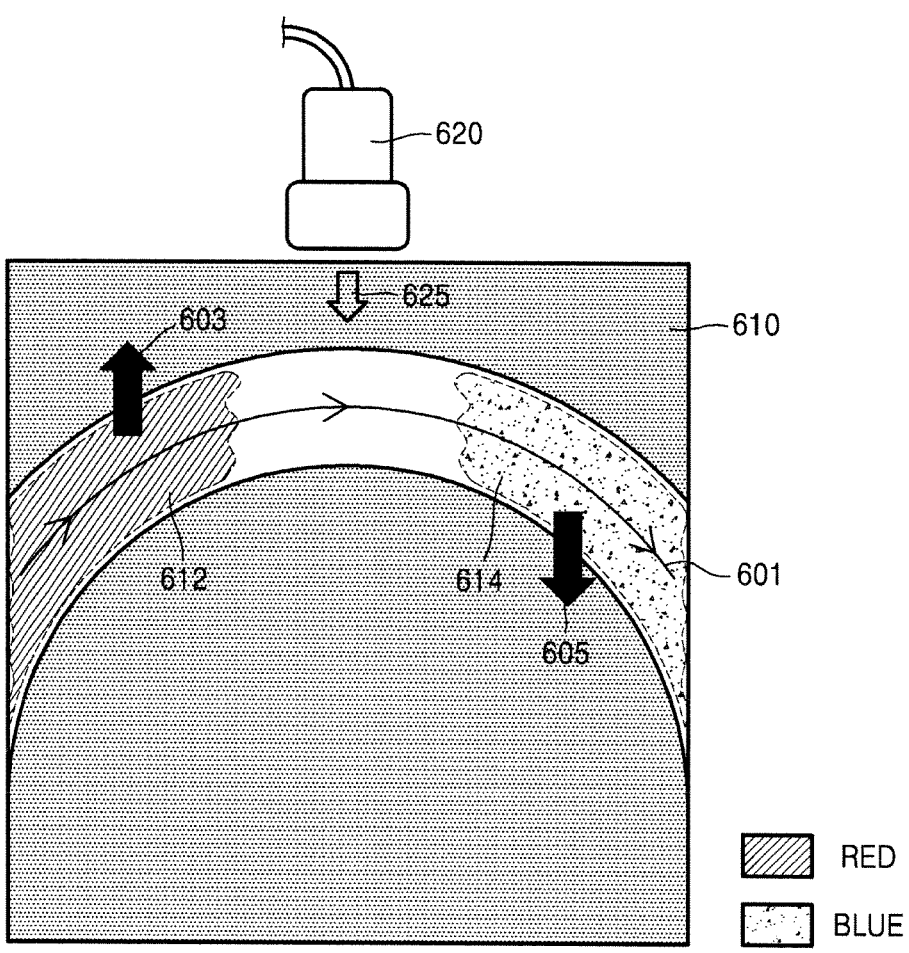
FIGS. 6A, 6B, 7A, and 7B are views illustrating a color Doppler image and a sound source marker that are displayed, according to embodiments of the present invention.
Figure 6B:
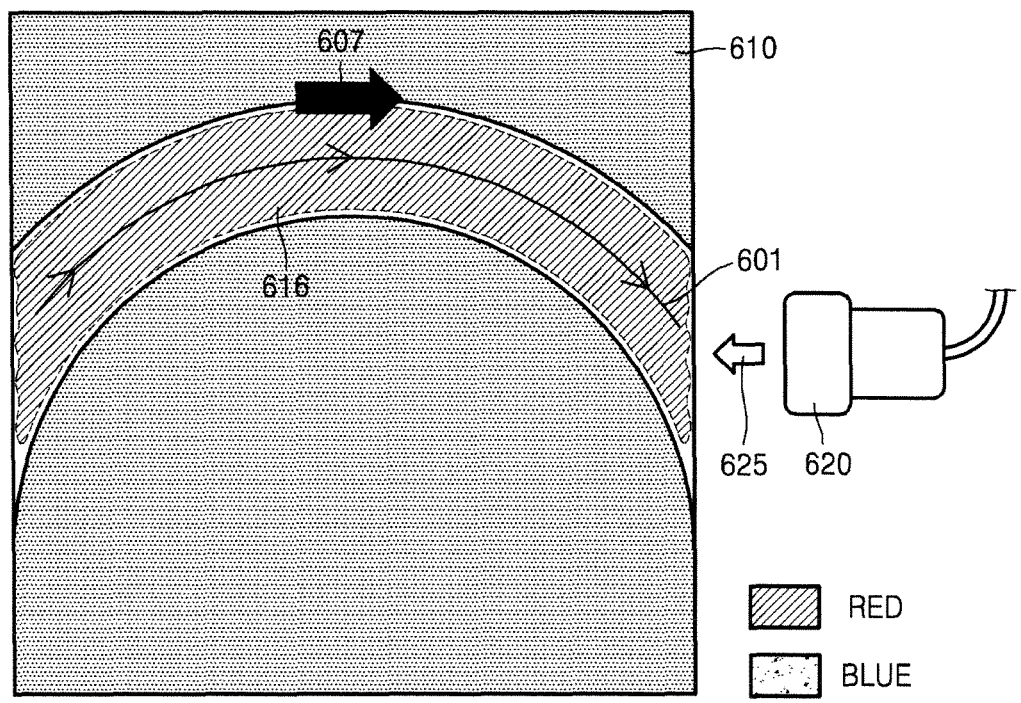

FIGS. 6A and 6B are views illustrating a color Doppler image and a sound source marker 620 that are displayed, according to an embodiment of the present invention.

In FIGS. 6A and 6B, an image 610 is a B mode image of an object, an arrow 601 is an actual direction of a bloodstream that flows in the object, and images 612, 614, 622, and 624 are color Doppler images. The arrow 601 and arrows 603, 605, and 607 may not be shown on a screen, but are shown herein for a better understanding of the present invention. Also, in FIGS. 6A and 6B, it is assumed that a center of a top surface of the image 610 is a reference position. However, the present embodiment is not limited thereto, and any of various positions on the screen may be determined as the reference position.

As shown in FIG. 6A, the apparatus 300 of FIGS. 6A and 6B may display the sound source marker 620 at a first position, and may display the color Doppler images 612 and 614 that are first color Doppler images generated in consideration of the first position.

The apparatus 300 may generate second Doppler data by correcting first Doppler data based on a result of comparison between the first position of the sound source marker 620 and the reference position on the screen. In detail, the apparatus 300 may obtain an angle between a line that connects the reference position and a predetermined point on the screen and a line that connects the predetermined point and the first position, and may generate the second Doppler data by correcting the first Doppler data based on the obtained angle. Although it is assumed in FIGS. 6A and 6B that a center of the image 610 of the object is the predetermined point on the screen, the present embodiment is not limited thereto.

As described above, since the arrow 601 indicating the actual direction of the bloodstream that flows the object is not actually shown on a color Doppler image that is displayed by an ultrasound system, a user predicts a direction of the bloodstream based on a position of the sound source marker 620 and a color of the color Doppler image.

The user may determine that a direction of the bloodstream of an area where the color Doppler image 612 is shown in red is a direction in which the bloodstream moves toward the sound source marker 620 as indicated by the arrow 603. Also, the user may determine that a direction of the bloodstream of an area where the color Doppler image 614 is shown in blue is a direction in which the bloodstream moves away from the sound source marker 620 as indicated by the arrow 605.

As shown in FIG. 6A, the apparatus 300 may display a position that becomes a basis of a relative velocity of the bloodstream expressed by a Doppler image by using the sound source marker 620 that has a probe-like shape. Alternatively, the apparatus 300 may display a transmission direction of an ultrasound beam that becomes a basis of a relative velocity of the bloodstream expressed by a Doppler image by using an arrow 625.

Herein, in the color Doppler image displayed by the apparatus 300, the bloodstream that moves toward a reference point is shown in red, and the bloodstream that moves away from the reference point is shown in blue. However, the present embodiment is not limited thereto, and a color allocated to each color Doppler image may be changed.

In an embodiment of the present invention, the apparatus 300 may map a velocity of the bloodstream to each of various colors and may store the velocity. The apparatus 300 may allocate a color corresponding to each calculated velocity of the bloodstream to the color Doppler image. The apparatus 300 may further display a color bar indicating mapping information between a velocity of the bloodstream and an allocated color on the screen. Also, the apparatus 300 may display a direction and a velocity of the bloodstream by using an arrow having any of various directions and sizes as well as colors.

Referring back to FIG. 6A, FIG. 6A illustrates that the sound source marker 620 is located at the reference position. The apparatus 300 may compare the first position of the sound source marker 620 with the reference position that is preset, and may determine that the first position and the reference position are the same according to a result of the comparison. Accordingly, the apparatus 300 may generate the first color Doppler image from the first Doppler data without passing through a separate process of processing the first Doppler data, based on the result of the comparison.

FIG. 6B illustrates that the sound source marker 620 is moved clockwise by 90° about the center of the image 610 to be displayed at the first position. The apparatus 300 may obtain an angle between a line that connects the center of the image 610 and the reference position and a line that connects the center of the image 610 and the first position of the sound source marker 620. The angle obtained in FIG. 6B is 90°. The apparatus 300 may generate the second Doppler data by correcting the first Doppler data based on the obtained angle. The apparatus 300 may generate and display a first Doppler data image 616 from the second Doppler data.

In FIG. 6B, the user may determine that a direction of the bloodstream corresponding to the color Doppler image 622 to which a red color is allocated is a direction in which the bloodstream moves toward the sound source marker 620, that is, moves from the left to the right on the screen, as indicated by the arrow 607.

As described above, in FIGS. 6A and 6B, the apparatus 300 may correct and output the Doppler data to display the color Doppler image that well shows bloodstream information without physically moving a probe that obtains real-time Doppler data of the object. Accordingly, in FIGS. 6A and 6B, the user using the apparatus 300 may select and receive the color Doppler image in which the bloodstream information is best shown in a desired view via a simple manipulation, without physically moving the probe.

In an embodiment of the present invention, the apparatus 300 may update and display the color Doppler image based on geometry transformation of the color Doppler image or a movement of the sound source marker 620. A method performed by the apparatus 300 to display an ultrasound image will now be explained in detail with reference to FIG. 4B.

As shown in FIG. 4B, the method may further include updating and displaying the color Doppler image based on geometry transformation of the color Doppler image or a movement of the sound source marker. Also, although not shown in FIG. 4B, the apparatus 300 may update bloodstream information indicated by the color Doppler image by further using at least one of power data including information about the amount of the bloodstream and Doppler data of a peripheral area around a predetermined area of the color Doppler image.

In an embodiment of the present invention, the apparatus 300 may reconstruct the color Doppler image based on a transformed geometry of the color Doppler image, a position of the sound source marker, and the Doppler data. Accordingly, the bloodstream that is not shown on the screen because an angle between the bloodstream and the ultrasound signal that is transmitted/received from the probe is 90° may also be displayed. Also, the apparatus 300 in FIG. 4B may check a flow and connection of the bloodstream which may not be checked in an original color Doppler image according to the movement of the sound source marker by using the updated color Doppler image.

Also, the apparatus 300 of an embodiment of the present invention may be used to generate the color Doppler image by further using the power data as well as color data included in the Doppler data. The color data included in the Doppler data indicates a velocity and a direction of the bloodstream, and the power data included in the Doppler data indicates the amount of the bloodstream. That is, the power data includes information about an amplitude of an echo signal based on the transmitted ultrasound signal, and the amplitude of the echo signal increases as a density of the bloodstream increases.

When an angle between a direction in which the probe transmits ultrasound signals or receives echo signals and a direction in which the bloodstream flows is about 90°, a sensitivity of the color data is very low. Accordingly, data for generating the color Doppler image of an area where an angle between a direction in which the probe transmits/receives ultrasound and a direction in which the bloodstream flows is about 90° may be insufficient. Hence, the apparatus 300 in FIG. 4B may provide bloodstream information by using the power data for an area where the sensitivity of the color data is very low.

In operation S441, the apparatus 300 may move the sound source marker displayed at the first position to a second position based on the user's input. The apparatus 300 may move the sound source marker from the first position to the second position along a predetermined path on the screen.

Figure 9B:
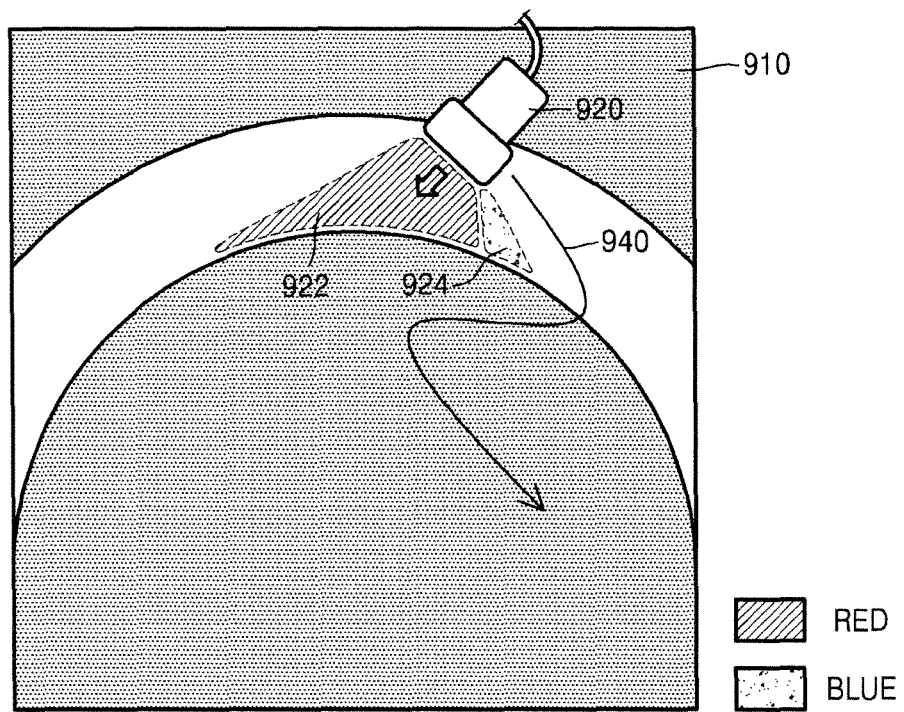

FIGS. 9A and 9B are views illustrating movement paths of a sound source marker 920 that is moved on a screen, according to embodiments of the present invention.

The apparatus 300 may move the sound source marker 920 along a path that is previously set around a color Doppler image. As shown in FIG. 9A, the apparatus 300 may move the sound source marker 920 along a predetermined path 930 around an image 910 of an object that is displayed on a screen. The apparatus 300 may move the sound source marker 920 based on a user input value through, for example, a mouse or a track ball.

Although the sound source marker 920 is moved around the image 910 having a quadrangular shape in FIG. 9A, the present embodiment is not limited thereto. For example, the sound source marker 920 may be moved along a circular path that is set based on a predetermined point on the image 910. In this case, the apparatus 300 may receive an angle by which the sound source marker 920 is to be moved along a desired path, and may move the sound source marker 920 to a position corresponding to the received angle.

Also, as shown in FIG. 9B, the apparatus 300 may move the sound source marker 920 to an arbitrary position on the image 910 based on the user's input. As indicated by an arrow 940 of FIG. 9B, the user may move the sound source marker 920 to a desired position on the image 910 as well as a peripheral area around the image 910.

In operation S443, the apparatus 300 in FIG. 4B may generate and display a second color Doppler image based the movement of the sound source marker.

For example, the apparatus 300 may obtain a first angle between a direction of the bloodstream expressed by the first color Doppler image and a reception direction of the ultrasound signal indicated by the sound source marker at the first position in order to generate the second color Doppler image.

Next, the apparatus 300 may obtain a second angle between the direction of the bloodstream expressed by the first color Doppler image and the reception direction of the ultrasound signal indicated by the sound source marker at the second position. The apparatus 300 may generate the second color Doppler image by correcting the first color Doppler image based on a difference between the first angle and the second angle.

Alternatively, the apparatus 300 may generate the second color Doppler image by correcting the first color Doppler image based on a result of the comparison between the first position and the second position. In detail, the apparatus 300 may obtain an angle between a line that connects the first position and a predetermined point on the screen and a line that connects the predetermined point and the second position. The apparatus 300 may generate the second color Doppler image by correcting the first color Doppler image based on the obtained angle. In this case, the predetermined point on the screen may be determined based on the user's input, or may be determined by a value that is previously stored in the apparatus 300. For example, the apparatus 300 may determine a center of the screen or a center of a color Doppler image as the predetermined point. For example, in order to generate the second color Doppler image by correcting the first color Doppler image based on the obtained angle, the method of correcting the color Doppler data described with reference to Equation 3 may be used.

As shown in FIG. 9A, the apparatus 300 may generate and display a second color Doppler image instead of first color Doppler images 912 and 914, as the sound source marker 920 is moved along a predetermined path 930. That is, the apparatus 300 may generate the second color Doppler image by allocating to a color Doppler image at least one color selected based on a relative velocity of the bloodstream that is newly calculated according to the movement of the sound source marker 920. The relative velocity of the bloodstream that varies according to the movement of the sound source marker 920 may be calculated by using Equations 1 through 3.

As shown in FIG. 9B, the apparatus 300 may generate, based on a position of the sound source marker 920, the second color Doppler image by using only at least a part of Doppler data.

As shown in FIG. 9B, when the probe is located inside a blood vessel, the apparatus 300 may predict that only Doppler data of at least a portion of the blood vessel may be obtained. The apparatus 300 may generate color Doppler images 922 and 924 of FIG. 9B, based on the Doppler data that is predicted to be obtained. Accordingly, according to the present embodiment, the apparatus 300 may more intuitively provide bloodstream information to the user by displaying the bloodstream information expressed by the color Doppler image by using the sound source marker.

In operation S451, the apparatus 300 in FIG. 4B may transform a geometry of the first color Doppler image based on the user's input. The geometry transformation refers to at least one of a movement, an expansion, a contraction, and a rotation of an image on the screen.

In operation S453, the apparatus 300 in FIG. 4B may generate and display the second color Doppler image based on the geometry transformation of the first color Doppler image.

For example, in order to generate the second color Doppler image by correcting the first color Doppler image based on the geometry transformation of the first color Doppler image, the method of correcting the color Doppler data described with reference to Equation 3 may be used.

Figure 7A:
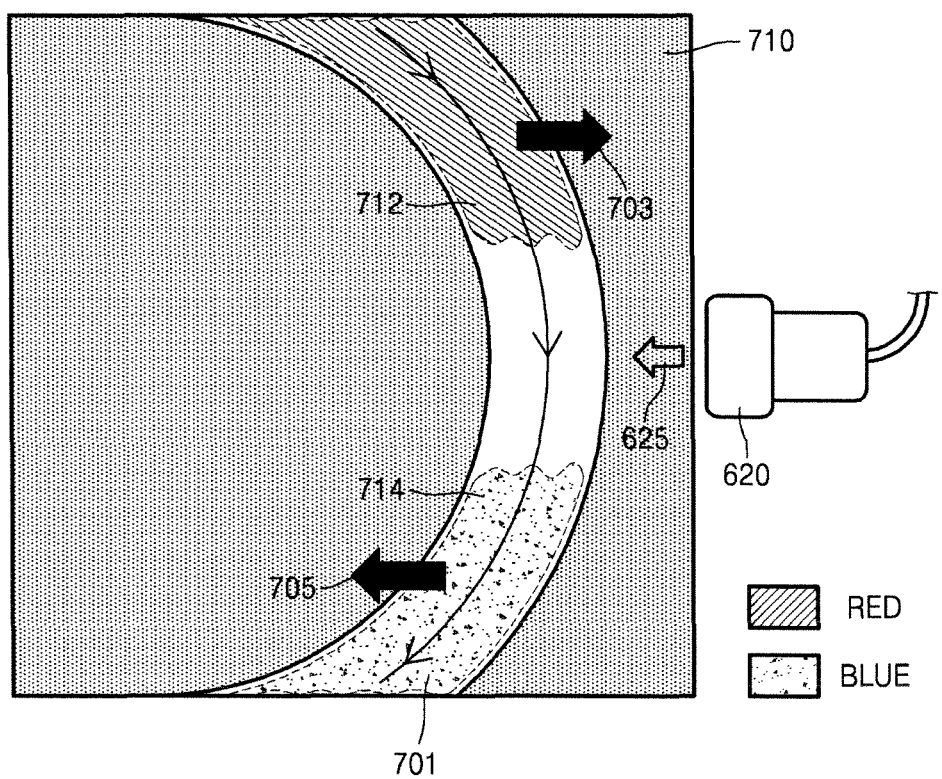
Figure 7B:
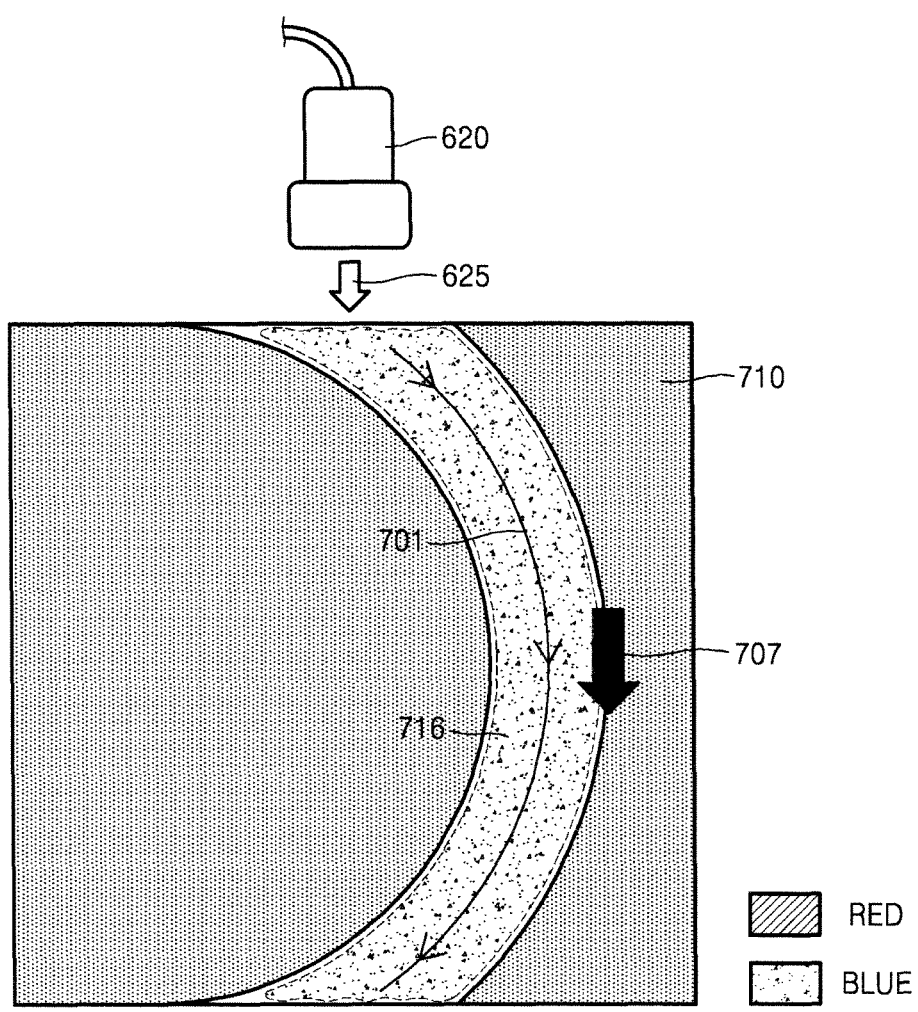

FIGS. 7A and 7B are views illustrating a color Doppler image and the sound source marker 620 that are displayed, according to another embodiment of the present invention.

In FIGS. 7A and 7B, an image 710 is a B mode image of an object, an arrow 701 indicates an actual direction of a bloodstream that flows in the object, and images 712, 714, and 716 are color Doppler images. The arrow 701 and arrows 703, 705, and 707 may not be shown on a screen, but are shown herein for better understanding of the present invention. Also, in FIGS. 7A and 7B, it is assumed that a center of a top surface of the image 610 of the object is a reference position. However, the present embodiment is not limited thereto, and any of various positions on the screen may be determined as the reference position.

FIG. 7A illustrates that the first color Doppler image 616 and the image 610 of FIG. 6B are rotated clockwise by 90° due to a user's manipulation.

As shown in FIG. 7A, when the first color Doppler image 616 of FIG. 6B is rotated clockwise by 90°, the apparatus 300 may generate and display the color Doppler images 712 and 714 that are second color Doppler images based on the rotation of the color Doppler image 616. The color Doppler images 712 and 714 may express a relative velocity of a bloodstream 701 based on a position of the sound source marker 620 of FIG. 7A.

Referring to FIG. 7A, the user may determine that a direction of the bloodstream expressed by the color Doppler image 712 to which a red color is allocated is a direction in which the bloodstream moves toward the sound source marker 620, that is, the bloodstream flows from the top to the bottom on the screen, as indicated by the arrow 703.

Also, referring to FIG. 7A, the user may determine that a direction of the bloodstream expressed by the color Doppler image 714 to which a blue color is allocated is a direction in which the bloodstream moves away from the sound source marker 620, that is, the bloodstream moves from the top to the bottom on the screen, as indicated by the arrow 705.

Accordingly, the apparatus 300 may provide to the user an accurate direction of the bloodstream irrespective of the geometry transformation of the color Doppler image.

FIG. 7B illustrates that a second color Doppler image is generated and displayed according to a movement of the sound source marker 620 on the assumption that the color Doppler images 712 and 714 of FIG. 7A are first color Doppler images.

As shown in FIG. 7B, when the sound source marker 620 of FIG. 7A is rotated clockwise by 90° about a center of the image 710, the apparatus 300 may generate the color Doppler image 716 that is a second color Doppler image based on the movement of the sound source marker 620. The color Doppler image 716 may express a relative velocity of the bloodstream 701 based on the sound source marker 620 of FIG. 7B.

Referring to FIG. 7B, the user may determine that a direction of the bloodstream corresponding to the color Doppler image 716 to which a blue color is allocated is a direction in which the bloodstream moves away from the sound source marker, that is, the bloodstream moves from the top to the bottom on the screen, as indicated by the arrow 707. Accordingly, in FIG. 7B, a direction of the bloodstream recognized by the user by using the color Doppler image 716 of FIG. 7B is the same as an actual direction of the bloodstream indicated by the arrow 701.

As shown in FIG. 7B, since the apparatus 300 reconstructs the color Doppler image according to the movement of the sound source marker and displays the reconstructed color Doppler image on the screen, the bloodstream that is not displayed in FIG. 7A may be displayed on the screen. The color Doppler image of FIG. 7B may be displayed at an area where an angle between a transmission/reception direction of ultrasound indicated by the sound source marker and a direction of the bloodstream is 90° and thus the color Doppler image is not displayed in FIG. 7A.

According to the present embodiment, the apparatus 300 may generate and display color Doppler images each expressing a relative velocity of the bloodstream to the probe at any of various positions by using Doppler data that is obtained from one physical position. Accordingly, irrespective of an actual position of the probe that obtains the Doppler data, the apparatus 300 may provide a more intuitive color Doppler image to the user.

Figure 8:
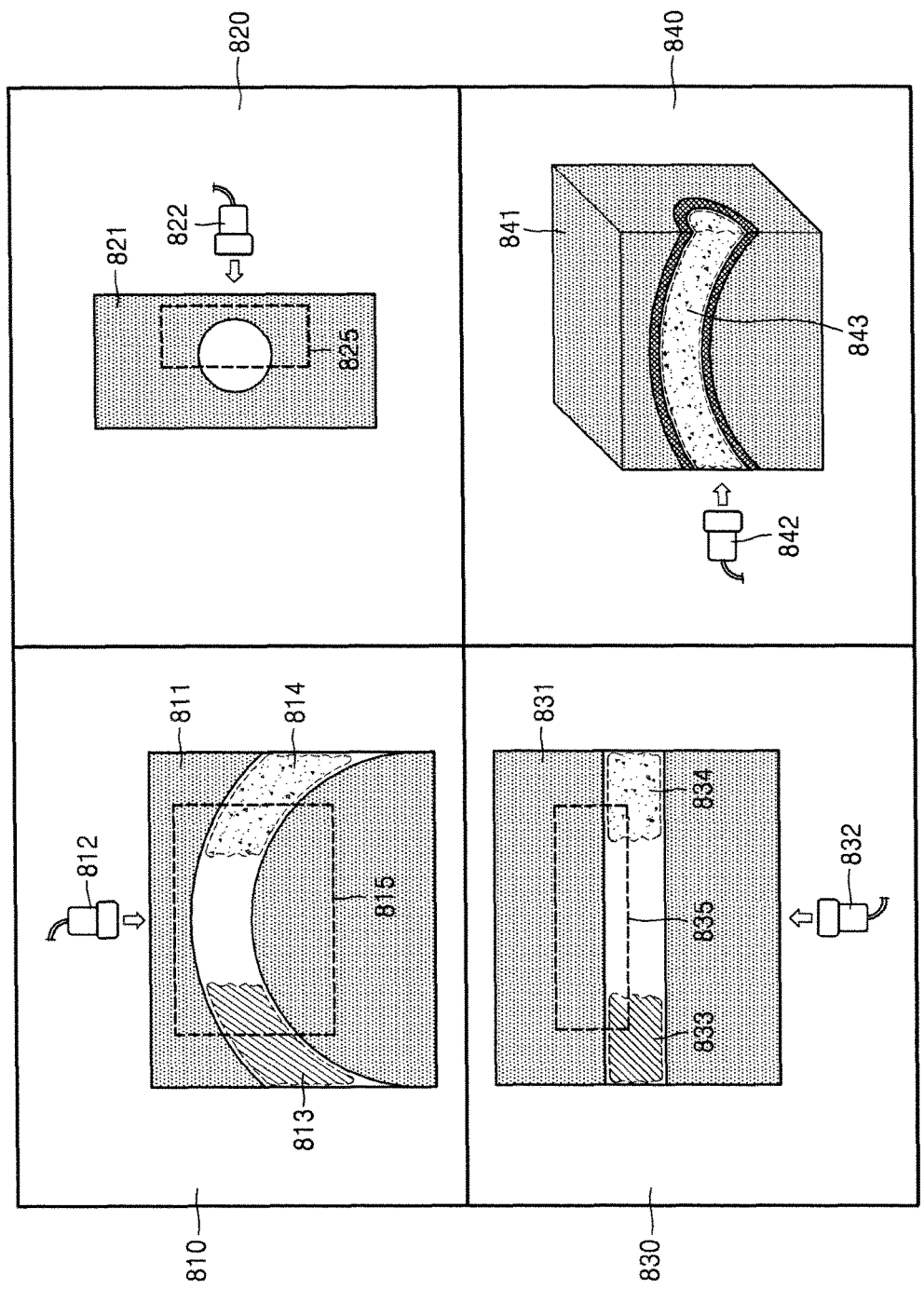
FIG. 8 is a view illustrating a plurality of color Doppler images that are generated based on positions of a plurality of sound source markers that are displayed, according to an embodiment of the present invention.

FIG. 8 is a view illustrating a plurality of Doppler images that are displayed and sound source markers that are displayed to correspond to the Doppler images, according to an embodiment of the present invention.

As shown in FIG. 8, the apparatus 300 may display a plurality of B mode images 811, 821, and 831 showing a plurality of cross-sections of an object in a plurality of areas 810, 820, 830, and 840 of a screen. The apparatus 300 may display color Doppler images 813, 814, 833, and 834 of the plurality of cross-sections of the object on the plurality of B mode images 811, 821, and 831.

Also, the apparatus 300 of FIG. 8 may support a 3D mode or a four-dimensional (4D) mode.

The term "3D mode" refers to a mode in which spatial information of the object is provided based on volume data of the object. The term "volume data" refers to a data set based on voxels. The term "4D mode" refers to a mode in which temporal information is provided along with spatial information of the object.

In the area 840 of FIG. 8, the apparatus 300 may display a 3D B mode image 841 of at least a part of the object, and may display a color Doppler image 843 on the displayed 3D B mode image 841.

The apparatus 300 may generate the 3D B mode image 841 corresponding to sizes of interest region setting interfaces 815, 825, and 835 on the plurality of B mode images 811, 821, and 831 indicating the plurality of cross-sections of the object. That is, a user may generate and display the 3D B mode image 841 corresponding to the interest region setting interfaces 815, 825, and 835, by adjusting the sizes of the interest region setting interfaces 815, 825, and 835 on the B mode images 811, 821, and 831.

The apparatus 300 in FIG. 8 may provide a plurality of sound source markers for a plurality of color Doppler images.

In the area 810 of FIG. 8, the apparatus 300 displays a sound source marker 812 at a position in the area 810. The apparatus 300 may display the color Doppler images 813 and 814 corresponding to the B mode image 811 on the B mode image 811 based on the predetermined position at which the sound source marker 812 is displayed. When geometries of the B mode image 811 and the color Doppler images 813 and 814 are transformed or the sound source marker 812 is moved based on the user's input, the apparatus 300 may update and display the color Doppler images 813 and 814.

In the area 820 of FIG. 8, when a transmission direction of an ultrasound signal indicated by a sound source marker 822 and a direction of a bloodstream are perpendicular to each other, a relative velocity of the bloodstream is 0, and thus there may be no color Doppler image corresponding to the B mode image 821. That is, any color Doppler image may not be displayed on the B mode image 821. In this case, the apparatus 300 in FIG. 8 may display a color Doppler image by transforming a geometry of the B mode image 821 or moving the sound source marker 822 based on the user's input.

In the area 830 of FIG. 8, the apparatus 300 displays a sound source marker 832 at a predetermined position. The apparatus 300 may display the color Doppler images 833 and 834 corresponding to the B mode image 831, on the B mode image 831, based on the predetermined position at which the sound source marker 832 is displayed. When geometries of the B mode image 831 and the color Doppler images 833 and 834 are transformed or the sound source marker 832 is moved based on the user's input, the apparatus 300 may update and display the color Doppler images 833 and 834.

In the area 840 of FIG. 8, the apparatus 300 may display the color Doppler image 843 corresponding to the 3D B mode image 841, on the 3D B mode image 841. The apparatus 300 displays a sound source marker 842 at a predetermined position. The apparatus 300 may generate and display the color Doppler image 843, based on the predetermined position at which the sound source marker 842 is displayed. When geometries of the 3D B mode image 841 and the color Doppler image 843 are transformed or the sound source marker 842 is moved based on the user's input, the apparatus 300 may update and display the color Doppler image 843.

For example, the apparatus 300 may move the sound source marker 842 along at least one of an x-axis, a y-axis, and a z-axis of the 3D B mode image 841 based on the user's input. Also, the apparatus 300 may rotate the 3D B mode image 841, or move the 3D B mode image 841 in a time domain based on the user's input. The apparatus 300 may update and display the color Doppler image 843 based on at least one of geometry transformation of a color Doppler image and a movement of a sound source marker.

The apparatus 300 in FIG. 8 may display a plurality of Doppler images at a plurality of areas on a screen, and displays a plurality of sound source markers at a plurality of positions of the plurality of areas, respectively. The apparatus 300 in FIG. 8 may move a sound source marker regarding to each of the plurality of Doppler images which correspond to a plurality of cross-sections of the object. And the apparatus 300 in FIG. 8 may transform a geometry of each of the plurality of Doppler images corresponding to the plurality of cross-sections of the object based on the user's input The user using the apparatus 300 in FIG. 8 may move a sound source marker to a desired position for each color Doppler image or may transform a geometry of the color Doppler image. Accordingly, the apparatus 300 in FIG. 8 may provide color Doppler images by which the user may intuitively recognize bloodstream information of a plurality of cross-sections of one object.

The apparatus 300 in FIG. 8 may enable the user to intuitively recognize bloodstream information in any of various views (for example, a standard view where the heart of a fetus is inspected, a standard diagnosis view recommended by the Association, or a view with which the user is most familiar). For example, the apparatus 300 may display a most appropriate color Doppler image in any of various views by moving a sound source marker or transforming a geometry of a displayed color Doppler image. Since the apparatus 300 may provide a direction of a bloodstream by displaying the most appropriate color Doppler image, the user of the apparatus 300 may intuitively recognize the direction of the bloodstream in the object.

According to a general ultrasound system, when a user manipulates a color Doppler image, the user may not obtain accurate information about a movement of a bloodstream. That is, there is a difference between an actual direction of the bloodstream and a direction of the bloodstream recognized by the user by using the color Doppler image.

In particular, when a second user loads a color Doppler image that is stored after being manipulated by a first user, the second user may have difficulties in intuitively recognizing a direction of a bloodstream expressed by the loaded color Doppler image.

However, according to the present embodiment, the apparatus 300 may provide a color Doppler image which the user may intuitively read by displaying the color Doppler image and displaying a sound source marker at a position corresponding to the color Doppler image.

Figure 5:
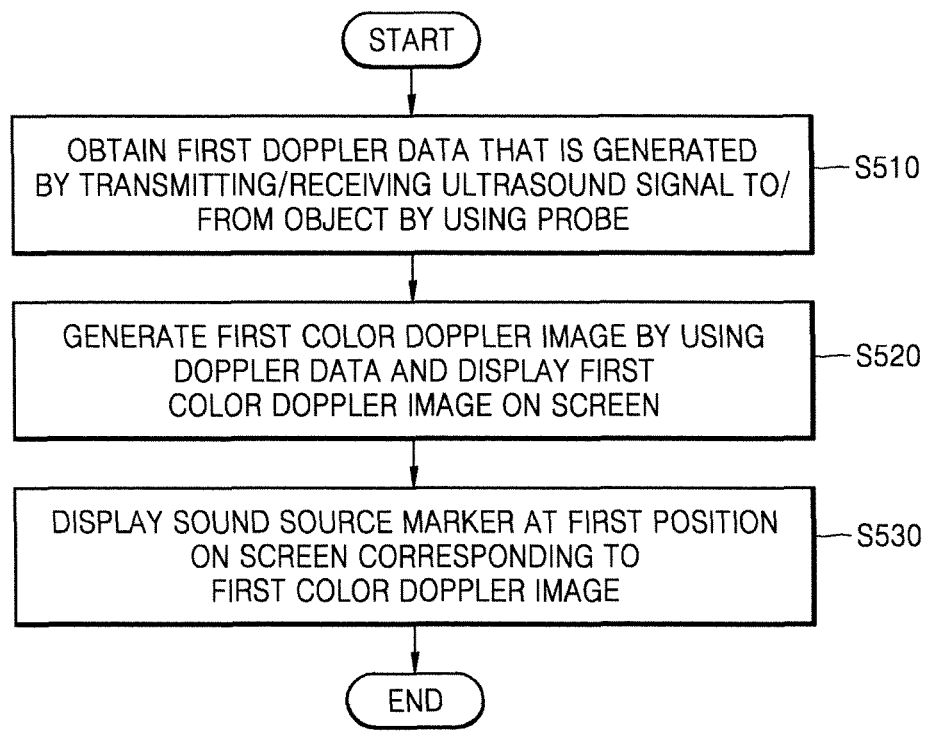
FIG. 5 is a flowchart of a method of displaying an ultrasound image, according to another embodiment of the present invention.

FIG. 5 is a flowchart of a method performed by the apparatus 300 to display an ultrasound image, according to another embodiment of the present invention.

In operation S510, the apparatus 300 obtains Doppler data of an object. The Doppler data obtained by the apparatus 300 is data that is generated by transmitting an ultrasound signal to the object and receiving an echo signal reflected from the object by using a probe.

In operation S520, the apparatus 300 generates a color Doppler image by using the Doppler data and displays the color Doppler image on a screen.

In operation S530, the apparatus 300 displays a sound source marker at a first position on the screen corresponding to the color Doppler image.

When the probe transmits/receives the ultrasound signal to/from the object in order to generate the Doppler data, the first position corresponding to the color Doppler image may refer to a position on the screen indicating an angle between a direction in which a bloodstream flows in the object and a direction in which the proves receives the ultrasound signal. For example, the apparatus 300 may determine the first position by analyzing the Doppler data or may extract information included in the Doppler data and may determine the first data based on the extracted information.

For convenience of explanation, the present embodiment will now be explained with reference to FIGS. 6A and 7A.

As shown in FIG. 6A, the apparatus 300 in FIG. 5 may display the sound source marker 620 at a position corresponding to the color Doppler images 612 and 614 that are first color Doppler images. The position corresponding to the color Doppler images 612 and 614 may refer to a position that becomes a basis of a relative velocity of a bloodstream expressed by the color Doppler images 612 and 614.

Also, when the image 610 and the color Doppler images 612 and 614 of FIG. 6A are rotated clockwise by 90° and stored, the apparatus 300 in FIG. 5 may output a screen as shown in FIG. 7A.

As shown in FIG. 7A, the apparatus 300 in FIG. 5 may display the sound source marker 620 at a position corresponding to the color Doppler images 712 and 714. In FIG. 7A, the sound source marker 620 may be displayed at a position that is rotated clockwise by 90° about a center of the image 610 in order to correspond to the color Doppler images 622 and 624 that are rotated by 90° and are stored.

Accordingly, a user in FIG. 7A may know based on the sound source marker 620 that the color Doppler images 712 and 714 express a relative velocity of the bloodstream with respect to the sound source marker 620. That is, the user may determine that a direction of the bloodstream corresponding to the color Doppler image 712 to which a red color is allocated is a direction in which the bloodstream moves toward the sound source marker 620, that is, the bloodstream moves from the left to the right on the screen, as indicated by the arrow 703. Also, the user may determine that a direction of the bloodstream corresponding to the color Doppler image 714 to which a blue color is allocated is a direction in which the bloodstream moves away from the sound source marker 620, that is, the bloodstream moves from the right to the left on the screen as indicated by the arrow 705.

Hence, according to the present embodiment, a direction of the bloodstream recognized by the user through the color Doppler images 712 and 714 of FIG. 7A is the same as an actual direction of the bloodstream.

As described above, the method and apparatus for displaying an ultrasound image of the present embodiment may display a color Doppler image and a sound source marker indicating a reference position and a direction for identifying the color Doppler image.

Figure 10:
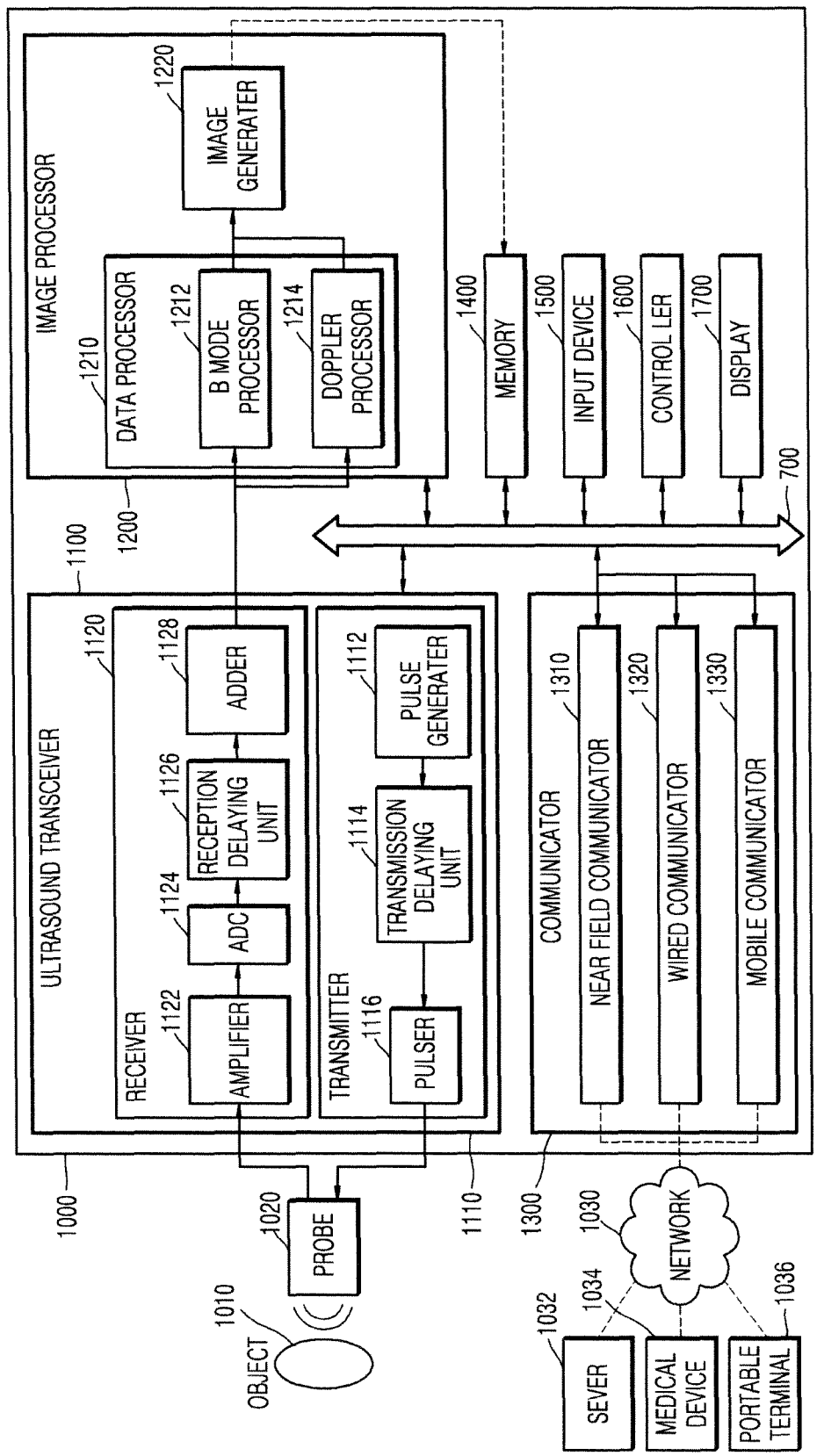
FIG. 10 is a block diagram illustrating an ultrasound system to which an apparatus for displaying an ultrasound image may be applied, according to an embodiment of the present invention.

FIG. 10 is a block diagram illustrating an ultrasound system 100 using an apparatus and method of displaying an ultrasound image, according to an embodiment of the present invention.

The method may be performed by the ultrasound system 1000 of FIG. 10, and the apparatus may be included in the ultrasound system 1000 of FIG. 10.

The apparatus 300 of FIGS. 3A and 3B may perform all or some of functions of the ultrasound system 100 of FIG. 10. The data obtainer 310 and the processor 330 of FIGS. 3A and 3B may correspond to a probe 1020, an ultrasound transceiver 1100, and an image processor 1200 of FIG. 10. The display 320 of FIGS. 3A and 3B may correspond to a display 1700 of FIG. 10. Also, the user input device 340 of FIGS. 3A and 3B may correspond to an input unit 1500 of FIG. 10.

The ultrasound system 1000 of FIG. 10 may include the probe 1020, the ultrasound transceiver 110, the image processor 1200, a communicator 1300, a memory 1400, the input device 1500, and a controller 1600 which may be connected to one another via a bus 700.

A transmitter 1110 applies a driving signal to the probe 1020, and includes a pulse generater 1112, a transmission delaying unit 114, and a pulser 1116. The pulse generator 1112 generates pulses for forming ultrasound according to a predetermined pulse repetition frequency (PRF), and the transmission delaying unit 114 applies a delay time to each of the pulses for determining a transmission directionality. Each pulse to which the delay time is applied corresponds to each of a plurality of piezoelectric vibrators included in the probe 1020. The pulser 1116 applies a driving signal (or a driving pulse) to the probe at a timing corresponding to each pulse to which the delay time is applied.

A receiver 1120 processes an echo signal received from the probe 1020 and generates ultrasound data. The receiver 1120 may include an amplifier 1122, an analog-to-digital converter (ADC) 1124, a reception delaying unit 1126, and a adder 1128. The amplifier 1122 amplifies the echo signal in each channel, and the ADC 1124 performs analog-to-digital conversion on the amplified echo signal. The reception delaying unit 1126 applies a delay time for determining a reception directionality to the converted echo signal, and generates ultrasound data by summing the echo signals processed by the reception delaying unit 1126.

The image processor 1200 generates and displays an ultrasound image by performing scan conversion on the ultrasound data that is generated by the ultrasound transmitting/receiver 1100.

A B mode processor 1212 extracts and processes a B mode component from the ultrasound data. An image generater 1220 may generate an ultrasound image that expresses an intensity of a signal by using a brightness based on the B mode component that is extracted by the B mode processor 1212.

Likewise, a Doppler processor 1214 may extract a Doppler component from the ultrasound data, and the image generater 1220 may generate a Doppler image that expresses a movement of an object 1010 by using a color or a waveform based on the extracted Doppler component.

The image generater 1220 of FIG. 8 may generate a 3D ultrasound image by performing volume rendering on volume data, and may also generate an elasticity image that shows a degree of deformation of the object 1010 according to pressure. Furthermore, the image generater 1220 may express various pieces of additional information as text or graphics on the ultrasound image. The generated ultrasound image may be stored in the memory 1400.

The communicator 1300 is wirelessly or wiredly connected to a network 1030 and communicates with an external device or a server. The communicator 1300 may transmit/receive data to/from a server or other medical devices in a hospital which are connected through a medical image information system (e.g., a PACS). Also, the communicator 1300 may transmit/receive data according to a digital imaging and communication in medicine (DICOM) standard.

The communicator 1300 may transmit/receive data related to diagnosis of the object 1010 such as an ultrasound image, ultrasound data, and Doppler data of the object 1010 through the network 1030, and may transmit/receive a medical image captured by another medical device such as a computed tomography (CT) system, a magnetic resonance imaging (MRI) system, or an X-ray system. Moreover, the communicator 1300 may receive information about a patient's diagnosis history or treatment schedule from the server and may use the information to diagnose the object 1010. Furthermore, the communicator 1300 may transmit/receive data to/from the patient or medical doctor's portable terminal as well as the server or the medical devices in the hospital.

The communicator 1300 may be wirelessly or wiredly connected to the network 1030, and may transmit/receive data to/from a server 1032, a medical device 1034, or a portable terminal 1036. The communicator 1300 may include at least one element that may communicate with an external device, for example, a near field communicator 1310, a wired communicator 1320, and a mobile communicator 1330.

The near field communicator 1310 is a module for near field communication within a predetermined distance. Examples of a near field communication technology may include, but are not limited to, wireless LAN, Wi-Fi, Bluetooth, Zigbee, Wi-Fi Direct (WFD), ultra wideband (UWB), infrared data association (IrDA), Bluetooth low energy (BLE), and near field communication (NFC).

The wired communicator 1320 is a module for communication using an electrical signal or an optical signal, and examples of a wired communication technology may include a pair cable, a coaxial cable, an optical fiber cable, and an Ethernet cable.

The mobile communicator 1330 transmits/receives a wireless signal to/from at least one of a base station, an external terminal, and a server through a mobile communication network. Examples of the wireless signal may include a voice call signal, a video call signal, and any of various types of data according to text/multimedia message transmission/reception.

The memory 1400 stores various pieces of information processed by the ultrasound system 1000. For example, the memory 1400 may store medical data related to diagnosis of the object 1010 such as ultrasound data or an ultrasound image that are input/output, and may store an algorithm or a program executed in the ultrasound system 1000.

The memory 1400 may be any of various types of storage media such as a flash memory, a hard disk, or an electrically erasable programmable read-only memory (EEPROM). Also, the ultrasound system 1000 may operate a web storage or a cloud server that performs a storage function of the memory 1400 in the web.

The input device 1500 is a unit that receives from a user data for controlling the ultrasound system 1000. The input device 1500 may include a hardware element such as, but not limited to, a keypad, a mouse, a touch panel, a touch screen, a track ball, or a jog switch. The input device 1500 may further include any of various input elements such as an electrocardiogram measurement module, a respiration measurement module, a voice recognition sensor, a gesture recognition sensor, a fingerprint recognition sensor, an iris recognition sensor, a depth sensor, or a distance sensor.

The controller 1600 controls an overall operation of the ultrasound system 1000. That is, the controller 1600 may control an operation between the probe 1020, the ultrasound transceiver 1100, the image processor 1200, the communicator 1300, the memory 1400, and the input device 1500 of FIG. 10.

Some or all of the probe 1020, the ultrasound transceiver 1100, the image processor 1200, the communicator 1300, the memory 1400, the input device 1500, and the controller 1600 may be operated by, but are not limited to, a software module, and some of the above elements may be operated by hardware. Also, at least one of the ultrasound transceiver 1100, the image processor 1200, and the communicator 1300 may be included in, but are not limited to, the controller 1600.

The one or more embodiments of the present invention may be embodied as a recording medium, e.g., a program module to be executed in computers, which include computer-readable commands. The computer-readable medium may include any usable medium that may be accessed by computers, volatile and non-volatile media, and detachable and non-detachable media. Also, the computer-readable medium may include a computer storage medium and a communication medium. The computer storage medium includes all of volatile and non-volatile media, and detachable and non-detachable media which are designed to store information including computer-readable commands, data structures, program modules, or other data. The communication medium includes computer-readable commands, a data structure, a program module, and other transmission mechanisms, and includes other information transmission media.

While the present invention has been particularly shown and described with reference to exemplary embodiments thereof, it will be understood by one of ordinary skill in the art that various changes in form and details may be made therein without departing from the spirit and scope of the present invention as defined by the following claims. Hence, it will be understood that the embodiments described above are not limiting of the scope of the invention. For example, each component described in a single type may be executed in a distributed manner, and components described distributed may also be executed in an integrated form.

The scope of the present invention is indicated by the claims rather than by the detailed description of the invention, and it should be understood that the claims and all modifications or modified forms drawn from the concept of the claims are included in the scope of the present invention.

What is claimed is:

1. A method of displaying an ultrasound image, the method comprising:
    obtaining first Doppler data that is generated by transmitting an ultrasound signal to an object and receiving an echo signal reflected from the object by using a probe;
    displaying a sound source marker indicating a sound source of the ultrasound signal which is transmitted and received by the probe at a first position on a screen;
    generating and displaying a first color Doppler image from the first Doppler data, in consideration of the first position;
    obtaining information about a first angle between a direction of the bloodstream expressed by the first color Doppler image and a reception direction of the ultrasound signal indicated by the sound source marker at the first position;
    changing a position of the sound source marker with respect to the first color Doppler image from the first position to a second position by a user input;
    obtaining information about a second angle between the direction of the bloodstream expressed by the first color Doppler image and the reception direction of the ultrasound signal indicated by the sound source marker at the second position;
    generating a second color Doppler image by correcting the first color Doppler image based on a difference between the first angle and the second angle; and
    displaying the second color Doppler image on the screen.

2. The method of claim 1, wherein the generating and displaying of the first color Doppler image comprises:
    generating second Doppler data from the first Doppler data based on a result of comparison between the first position and a reference position on the screen; and
    generating the first color Doppler image from the second Doppler data.

3. The method of claim 1, further comprising:
    performing at least one of a movement, an expansion, a contraction, and a rotation of the object in the first color Doppler image on the screen with respect to the sound source marker.

4. The method of claim 1, wherein the screen comprises a plurality of areas at which a plurality of Doppler images are displayed,
    wherein the displaying of the sound source marker at the first position comprises displaying a plurality of sound source markers at a plurality of positions of the plurality of areas, respectively, and the generating and displaying of the first color Doppler image comprises generating and displaying a plurality of color Doppler images of a plurality of cross-sections of the object from the first Doppler data based on the plurality of positions of the plurality of sound source markers.

5. The method of claim 1, wherein the generating and displaying of the first color Doppler image comprises:
generating a three-dimensional (3D) brightness (B) mode image of at least a part of the object based on volume data of the object; and
displaying the first color Doppler image on the 3D B mode image.

6. The method of claim 5, further comprising:
moving the sound source marker displayed at the first position to a second position along at least one of an x-axis, a y-axis, and a z-axis of the 3D B mode image based on a user's input; and
generating a second color Doppler image based on the movement of the sound source marker and displaying the second color Doppler image on the 3D B mode image.

7. The method of claim 1,
wherein the first position forms an angle between a direction in which a bloodstream flows in the object and a direction in which the probe receives the echo signal.

8. An ultrasound imaging apparatus comprising:
a probe configured to obtain first Doppler data that is generated by transmitting an ultrasound signal to an object and receiving an echo signal reflected from the object;
a display screen;
a user input device; and
a processor configured to:
control the display screen to display a sound source marker indicating a sound source of the ultrasound signal which is transmitted and received by the probe at a first position on the display screen,
generate a first color Doppler image from the first Doppler data in consideration of the first position,
obtain information about a first angle between a direction of the bloodstream expressed by the first color Doppler image and a reception direction of the ultrasound signal indicated by the sound source marker at the first position,
change a position of the sound source marker with respect to the first color Doppler image from the first position to a second position by a user input,
obtain information about a second angle between the direction of the bloodstream expressed by the first color Doppler image and the reception direction of the ultrasound signal indicated by the sound source marker at the second position,
generate a second color Doppler image by correcting the first color Doppler image based on a difference between the first angle and the second angle, and
control the display screen to display the second color Doppler image on the display screen.

9. The apparatus of claim 8, wherein the processor is further configured to generate second Doppler data from the first Doppler data based on a result of comparison between the first position and a reference position on the screen, and generate the first color Doppler image from the second Doppler data.

10. The apparatus of claim 8, wherein the processor is further configured to perform at least one of a movement, an expansion, a contraction, and a rotation of the object in the first color Doppler image on the screen.

11. The apparatus of claim 8, wherein the processor is further configured to control the display screen to display a plurality of Doppler images at a plurality of areas on a screen, and display a plurality of sound source markers at a plurality of positions of the plurality of areas, respectively,
wherein the processor is further configured to generate a plurality of color Doppler images of a plurality of cross-sections of the object from the first Doppler data based on the plurality of positions of the plurality of sound source markers.

12. The apparatus of claim 8, wherein the processor is further configured to generate a three-dimensional (3D) brightness (B) mode image of at least a part of the object based on volume data of the object, and control the display screen to display the first color Doppler image on the 3D B mode image.

13. The apparatus of claim 12,
wherein the processor is further configured to move the sound source marker displayed at the first position to a second position along at least one of an x-axis, a y-axis, and a z-axis of the 3D B mode image, based on the received user's input, and generate the second color Doppler image based on the movement of the sound source marker, and control
the display screen to display the second color Doppler image on the 3D B mode image.

14. The apparatus of claim 8,
wherein the first position forms an angle between a direction in which a bloodstream flows in the object and a direction in which the probe receives the echo signal.

15. A non-transitory computer-readable recording medium having embodied thereon a program that, when executed by a processor, performs the steps of:
obtaining first Doppler data that is generated by transmitting an ultrasound signal to an object and receiving an echo signal reflected from the object by using a probe;
causing display of a sound source marker indicating a sound source of an ultrasound signal which is transmitted and received by the probe at a first position on a screen; and
generating and causing display of a first color Doppler image from the first Doppler data, in consideration of the first position;
obtaining information about a first angle between a direction of the bloodstream expressed by the first color Doppler image and a reception direction of the ultrasound signal indicated by the sound source marker at the first position;
changing a position of the sound source marker with respect to the first color Doppler image from the first position to a second position by a user input
obtaining information about a second angle between the direction of the bloodstream expressed by the first color Doppler image and the reception direction of the ultrasound signal indicated by the sound source marker at the second position;
generating a second color Doppler image by correcting the first color Doppler image based on a difference between the first angle and the second angle; and
causing display of the second color Doppler image on the screen.

* * * * *